United States Patent
Staas et al.

(10) Patent No.: US 6,312,731 B1
(45) Date of Patent: *Nov. 6, 2001

(54) RAPID RELEASE ENCAPSULATED BIOACTIVE AGENTS FOR INDUCING OR POTENTIATING AN IMMUNE RESPONSE AND METHODS OF USING THEREOF

(75) Inventors: Jay K. Staas, Alabaster; Thomas R. Tice, Birmingham, both of AL (US); Syamal Raychaudhuri, Mercer Island; Paul R. Sleath, Seattle, both of WA (US)

(73) Assignees: Southern Research Institute, Birmingham, AL (US); Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 19 days.

(21) Appl. No.: 09/143,162

(22) Filed: Aug. 28, 1998

Related U.S. Application Data

(60) Provisional application No. 60/057,363, filed on Aug. 29, 1997.

(51) Int. Cl.$^7$ ................ A61F 2/02; A61K 9/50; B32B 5/16
(52) U.S. Cl. ............ 424/501; 424/426; 424/502; 428/402.21
(58) Field of Search .................. 424/423, 426, 424/497, 498, 501, 502; 428/402.21

(56) References Cited

U.S. PATENT DOCUMENTS

| | | | |
|---|---|---|---|
| 5,529,777 | * | 6/1996 | Andrianov et al. ............ 424/184.1 |
| 5,650,173 | | 7/1997 | Ramstack et al. . |
| 5,654,008 | | 8/1997 | Herbert et al. . |
| 5,656,297 | | 8/1997 | Bernstein et al. . |

FOREIGN PATENT DOCUMENTS

WO 92/19263    11/1992   (WO) .

OTHER PUBLICATIONS

Newman et al., "Biodegradable Poly–(D,L–Lactide–c–o–Glycolic Acid) Microspheres as Antigen Delivery Systems for the Selective Induction of Cellular Immune Responses Against Synthetic Peptides," Pharmaceutical Research, vol. 13, No. 9 (1996).

Maloy et al., "Induction of Muscosal and Systemic Immune Responses By Immunization With Ovalbumin Entrapped In Poly(lactide–co–glycolide) Microparticles", Immunology, 81, pp. 661–667 (1994).

Men et al., "Induction of Sustained and Elevated Immune Responses To Weakly Immunogenic Synthetic Malarial Peptides By Encapsulation In Biodegradable Polymer Microspheres", Vaccine, vol. 14, No. 15, pp. 1442–1450 (1996).

Partidos et al., "Mucosal Immunization With A Measles Virus CTL Epitope Encapsulated In Biodegradable PLG Microparticles", Journal of Immunological Methods 195, pp. 135–138 (1996).

* cited by examiner

*Primary Examiner*—Carlos A. Azpuru
(74) *Attorney, Agent, or Firm*—Needle & Rosenberg, P.C.

(57) ABSTRACT

A composition for inducing or potentiating an immune response, preferably a CTL, T helper cell, or neutralizing antibody response in a subject, comprising an antigen and/or a non-antigen bioactive agent capable of inducing or potentiating such an immune response encapsulated in a polymeric composition, wherein the polymeric composition comprises a blend of (a) a polymer present in an amount sufficient to provide structural integrity to the polymeric composition, and (b) a rapidly biodegradable component, a rapidly dissolving component, a rapidly swelling component, or a component that causes osmotic rupture of the encapsulated polymeric composition is disclosed. Single polymer compositions for achieving such an immune response are also disclosed. Methods for inducing or potentiating a CTL, T helper cell or neutralizing antibody response using the above-identified compositions are disclosed.

56 Claims, 10 Drawing Sheets

Figure 1:
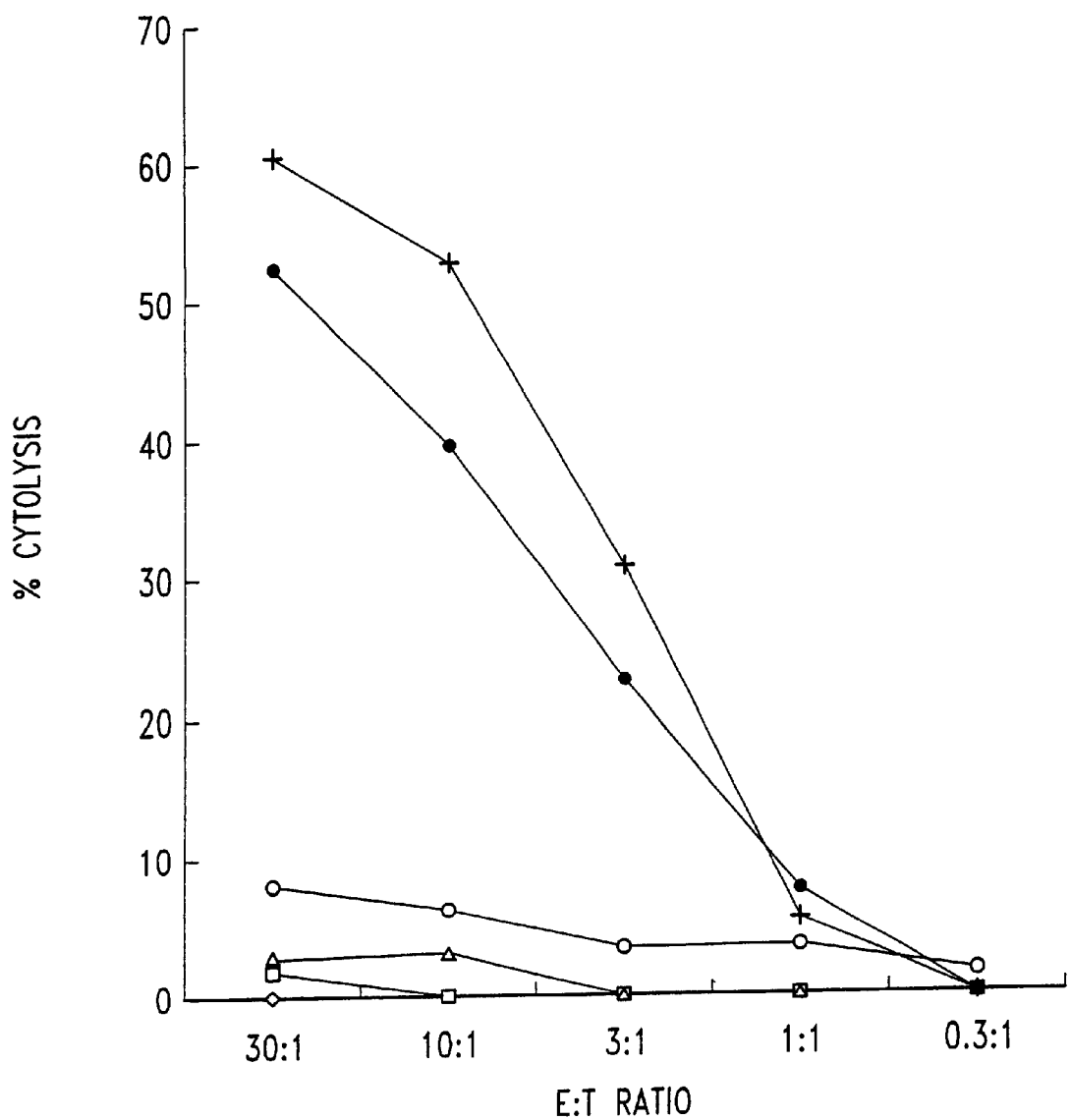

RAPID RELEASE ENCAPSULATED BIOACTIVE AGENTS FOR INDUCING OR POTENTIATING AN IMMUNE RESPONSE AND METHODS OF USING THEREOF

The present application claims priority from U.S. Provisional Application No. 60/057,363, Aug. 29, 1997, which application is incorporated herein by reference in its entirety.

FIELD OF THE INVENTION

The present invention provides bioactive agents encapsulated in a rapidly releasing polymeric composition capable of inducing or potentiating an immune response and methods for their use.

BACKGROUND OF THE INVENTION

Cytotoxic T lymphocytes (CTL) play a major role in both regulation of tumor growth and protection against infectious diseases. They recognize antigenic peptides, bound to MHC class I molecules, from either tumor associated antigens or antigens from infectious agents. These peptides are generated in the cytosol and then transferred into the endoplasmic reticulum where they bind to MHC class I molecules. The peptide-class I complex is then transported to the cell surface where it is displayed to CTLs. In order to induce or potentiate CTL responses, it is therefore generally necessary to introduce protein antigens into the cytoplasm.

One approach that has been used to introduce antigens into the MHC class I pathway is the use of recombinant infectious agents such as vaccinia virus, adenovirus, Listeria monocytogenes and other similar vectors. However, a number of safety concerns need to be addressed before infectious agents can have widespread acceptance in vaccine use. Other approaches involve conventional adjuvants, such as alum, or oil based materials, such as Montanide 720 or TiterMax, to deliver antigens in the form of emulsions. However, alum produces weak and variable CTL responses and typically is not effective at inducing immune responses to weak antigens. Oil based adjuvants present a toxicity issue that has not yet been satisfactorily addressed. Consequently, a number of new adjuvants, such as QS21 and AF, have been developed and demonstrate in some cases that they are capable of inducing CTL mediated responses. However, there remains a clear need for a delivery system that is biologically safe while being capable of inducing strong CTL responses against tumor or infectious disease antigens.

The use of microencapsulation to protect sensitive bioactive agents from degradation has become well known. Typically, a bioactive agent is encapsulated within a protective wall material, usually polymeric in nature. The polymer used to encapsulate the bioactive agent is typically a single copolymer or homopolymer. Example polymers for sutures, prostheses and other medical devices as well as drug and antigen carriers are polylactide, polyglycolide, and poly(lactide-co-glycolide). These polymers and copolymers have been utilized to elicit MHC class II responses. For example, U.S. Pat. No. 5,417,986 to Reid et al. discloses the delivery of an antigen using poly(lactide-co-glycolide) microspheres. The microencapsulated antigen was injected into rabbits to produce an antibody response.

Ertl et al. (Vaccine, 1996, vol. 14, no. 9, Peyer's patch 879–885) discloses the use of poly(lactide-co-glycolide) polymers to incorporate linear peptide epitopes as peptide vaccines in order to elicit a MHC class II responses. Hermann et al. (International Journal of Pharmaceutics, 1995, 126, Peyer's patch 129–138) discloses the preparation of biodegradable polyester microspheres of polylactide and poly(lactide-co-glycolide)) containing somatostatin, which is a peptide drug. Thomasin et al. (Journal of Controlled Release, 1996, 41, Peyer's patch 131–145) discloses the degradation of poly(lactide) and poly(lactide-co-glycolide) microspheres and the concurrent release of a natural and a synthetic antigen for eliciting an immune response in mice.

A combination of two or more types of polymeric microspheres that contain a bioactive agent have been made. Such combination microspheres have been shown to elicit MHC class II responses also. Men et al. (Vaccine, 1995, 13(7), Peyer's patch 683–689) discloses the combination, or a mixture, of microspheres that were separately prepared from poly(lactide) and poly(lactide-co-glycolide) respectively with a molecular weight ranging from 12,000 to 129,000 daltons, which contained tetanus toxoid as the bioactive agent. The microspheres elicited a T cell proliferative response and antibody production.

Although previous work in immunological delivery research has achieved delivery of strong antigens to elicit an immune response, such as a CTL response, there is a great need for delivery systems capable of effecting a CTL response to less immunogenic antigens. Such systems can be utilized to develop highly useful, effective vaccines. The present invention fills this need very effectively by providing compositions of an antigen encapsulated in microspheres that rapidly release the antigen once taken up by the cell to elicit a strong CTL response. The compositions are capable of inducing an immune response even against weakly immunogenic antigens. The inventive encapsulated antigens are thus capable of inducing an immune response and, in particular, a CTL response, sufficient for use as effective vaccines. Furthermore, the present invention also fulfills the need for effective vaccines by providing a means to potentiate any immune response by administering to a subject generating the immune response a bioactive agent capable of adjuvant function encapsulated in a microsphere that rapidly releases the bioactive agent. The improved delivery of the bioactive agent stimulates an improved immune response.

SUMMARY OF THE INVENTION

The present invention provides bioactive agents encapsulated in a rapidly releasing polymeric composition capable of inducing or potentiating an immune response and methods for their use.

In accordance with the purpose(s) of this invention, as embodied and broadly described herein, this invention, in one aspect, relates to a composition for inducing a CTL response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a CTL response is measurable within fourteen days of a single administration at a level of at least 30% cytotoxicity. The composition can further comprise a non-antigen bioactive agent capable of inducing or potentiating an immune response, or in particular, a CTL response. The non-antigen bioactive agent can be encapsulated in the polymeric composition or the non-antigen bioactive agent can be present in the composition unencapsulated.

The present invention also provides a composition for inducing a T helper cell response in a subject, comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a T helper cell response is measurable within fourteen days of a single administration at a level of at least two-fold over background as measured by T cell proliferation or cytokine induction.

Also provided is a composition for inducing a neutralizing antibody response in a subject, comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within fourteen days of a second or subsequent administration.

Additionally provided is a composition for inducing a neutralizing antibody response in a subject, comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within thirty days of a single administration.

Also provided is a composition for potentiating a preexisting CTL response to an antigen in a subject, comprising a bioactive agent encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated CTL response is measurable within fourteen days of a single administration at a level greater than the preexisting CTL response. The bioactive agent can comprise an antigen to which the immune response is induced or potentiated or a nucleic acid functionally encoding such an antigen.

Further provided is a composition for potentiating a preexisting T helper cell response to an antigen in a subject, comprising a bioactive agent encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated T helper cell response is measurable within fourteen days of a single administration at a level greater than the preexisting T helper cell response.

Additionally provided is a composition for potentiating a preexisting neutralizing antibody response to an antigen in a subject, comprising a bioactive agent encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is measurable within fourteen days of a second or subsequent administration at a level greater than the preexisting neutralizing antibody response.

Further provided is a composition for potentiating a neutralizing antibody response to an antigen in a subject, comprising a bioactive agent encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within thirty days of a single administration in at a level greater than the preexisting neutralizing antibody response.

The present invention further provides a method of inducing a CTL response in a subject, comprising administering to the subject an effective amount of a composition comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a CTL response is measurable within fourteen days of a single administration at a level of at least 30% cytotoxicity, thereby inducing the CTL response in the subject.

The present invention also provides a method of inducing a T helper cell response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a T helper cell response is measurable within fourteen days of a single administration at a level of at least two-fold over background as measured by T cell proliferation or cytokine induction, thereby inducing the T helper cell response in the subject.

Also provided is a method of inducing a neutralizing antibody response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within fourteen days of a second or subsequent administration, thereby inducing the neutralizing antibody response in the subject.

Additionally provided is a method of inducing a neutralizing antibody response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within thirty days of a single administration, thereby inducing the neutralizing antibody response in the subject.

Further provided by the present invention is a method of potentiating a preexisting CTL response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated CTL response is measurable within fourteen days of a single administration at a level greater than the preexisting CTL response, thereby potentiating the preexisting CTL response in the subject.

The present invention further provides a method of potentiating a preexisting T helper cell response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated T helper cell response is measurable within fourteen days of a single administration at a level greater than the preexisting T helper cell response, thereby potentiating the preexisting T helper response in the subject.

Further provided by the present invention is a method of potentiating a preexisting neutralizing antibody response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within fourteen days of a second or subsequent administration at a level greater than the preexisting neutralizing antibody response, thereby potentiating the preexisting neutralizing antibody response in the subject.

The present invention also provides a method of potentiating a neutralizing antibody response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within thirty days of a single administration at a level greater than the preexisting neutralizing antibody response, thereby potentiating the preexisting neutralizing antibody response in the subject.

The invention further relates to a method of inducing a CTL, T helper or neutralizing antibody response in a subject, comprising administering to the subject an effective amount of a composition comprising an antigen or a nucleic acid encoding the antigen, encapsulated in a polymeric composition, wherein the polymeric composition comprises a biodegradable polymer with a molecular weight of less than or equal to 7000 daltons.

The invention further relates to a method of inducing a CTL, T helper or neutralizing antibody response in a subject comprising administering to the subject an effective amount of a composition comprising an antigen or a nucleic acid encoding the antigen, encapsulated in a polymeric composition, wherein the polymeric composition comprises a rapidly biodegradable polymer with an inherent viscosity of less than 0.4 dL/g.

The invention further relates to a method for inducing a CTL, T helper cell or neutralizing antibody response in a subject, comprising administering to the subject an effective amount of a composition comprising an antigen or nucleic acid encoding the antigen, encapsulated in a polymeric composition, wherein the polymeric composition comprises an unblocked polymer of poly(lactide-co-glycolide), polylactide or polyglycolide.

The invention further relates to a method of potentiating a CTL, T helper or neutralizing antibody response in a subject, comprising administering to the subject an effective amount of a composition comprising a bioactive agent encapsulated in a polymeric composition, wherein the polymeric composition comprises a biodegradable polymer with a molecular weight of less than or equal to 7000 daltons.

The invention further relates to a method of potentiating a CTL, T helper or neutralizing antibody response in a subject, comprising administering to the subject an effective amount of a composition comprising a bioactive agent encapsulated in a polymeric composition, wherein the polymeric composition comprises a biodegradable polymer with an inherent viscosity of less than 0.4 dL/g.

The invention further relates to a method for potentiating a CTL, T helper cell or neutralizing antibody response in a subject, comprising a bioactive agent capable of potentiating a CTL, T helper cell or neutralizing antibody response encapsulated in a polymeric composition, wherein the polymeric composition comprises an unblocked polymer of poly(lactide-co-glycolide), polylactide or polyglycolide.

The invention further relates to a composition for inducing a CTL, T helper or neutralizing antibody response in a subject, comprising an effective amount of a composition comprising an antigen or a nucleic acid encoding the antigen, encapsulated in a polymeric composition, wherein the polymeric composition comprises a biodegradable polymer with a molecular weight of less than or equal to 7000 daltons.

The invention further relates to a composition for inducing a CTL, T helper or neutralizing antibody response in a subject, comprising an effective amount of a composition comprising an antigen or a nucleic acid encoding the antigen, encapsulated in a polymeric composition, wherein the polymeric composition comprises a biodegradable polymer with an inherent viscosity of less than 0.4 dL/g.

The invention further relates to a composition for inducing a CTL, T helper cell or neutralizing antibody response in a subject, comprising an effective amount of a composition comprising an antigen or nucleic acid encoding the antigen, encapsulated in a polymeric composition, wherein the polymeric composition comprises an unblocked polymer of poly(lactide-co-glycolide), polylactide or polyglycolide.

The invention further relates to a composition for potentiating a CTL, T helper or neutralizing antibody response in a subject, comprising an effective amount of a composition comprising a bioactive agent encapsulated in a polymeric composition, wherein the polymeric composition comprises a biodegradable polymer with a molecular weight of less than or equal to 7000 daltons.

The invention further relates to a composition for potentiating a CTL, T helper or neutralizing antibody response in a subject, comprising an effective amount of a composition comprising a bioactive agent encapsulated in a polymeric composition, wherein the polymeric composition comprises a biodegradable polymer with an inherent viscosity of less than 0.4 dL/g.

The invention further relates to a composition for potentiating a CTL, T helper cell or neutralizing antibody response in a subject, comprising an effective amount of a composition comprising a bioactive agent encapsulated in a polymeric composition, wherein the polymeric composition comprises an unblocked polymer of poly(lactide-co-glycolide), polylactide or polyglycolide.

Additional advantages of the invention will be set forth in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 1 shows the loading of antigen by Ova/PLG1 microspheres into the class I MHC pathway. PLG1 microspheres comprise a single polymer.

FIGS. 2*a–c* show the in vivo induction of CTLs by Ova encapsulated in PLG1 microspheres.

FIGS. 3*a–e* shows the kinetic study of Ova/PLG1 immunization.

FIGS. 4*a–c* show the in vivo induction of CTLs by the P815-1 peptide encapsulated in PLG1 microspheres.

FIG. 5 shows the induction of anti-tumor immunity in mice immunized with P815-1/PLG1 microspheres.

FIGS. 6*a–i* show anti-Ova induction of Ova encapsulated using blend component systems of this invention.

FIGS. 7*a–b* show the % cytotoxicity obtained using two microsphere preparations.

DETAILED DESCRIPTION OF THE INVENTION

The present invention may be understood more readily by reference to the following detailed description of preferred embodiments of the invention and the Examples included therein.

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

BLEND AND SINGLE COMPONENT COMPOSITIONS

One aspect of the invention relates to compositions for inducing immune responses in a subject. Specifically, provided is a composition for inducing a CTL response in a subject, comprising a bioactive agent, such as an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition, The polymeric composition can further provide kinetics of antigen or nucleic acid release such that a CTL response is measurable within fourteen days of a single administration at a level of at least 30% cytotoxicity. The composition can further comprise a non-antigen bioactive agent capable of inducing or potentiating an immune response, or in particular, a CTL response. The non-antigen bioactive agent can be encapsulated in the polymeric composition or the non-antigen bioactive agent can be present in the composition unencapsulated.

The present invention also provides a composition for inducing a T helper cell response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a T helper cell response is measurable within fourteen days of a single administration at a level of at least two-fold over background as measured by T cell proliferation or cytokine induction.

Also provided is a composition for inducing a neutralizing antibody response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within fourteen days of a second or subsequent administration. The method can further comprise a second administration of the antigen wherein the antigen is either encapsulated in the composition or not encapsulated in the composition.

Additionally provided is a composition for inducing a neutralizing antibody response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within thirty days of a single administration.

In each composition of the present invention, whether for inducing or potentiating an immune response, the composition can further comprise a non-antigen bioactive agent capable of inducing or potentiating an immune response, or in particular, a CTL response, a T helper cell response, and/or a neutralizing antibody response. The non-antigen bioactive agent can be encapsulated in the polymeric composition. Alternatively or additionally, a soluble or non-soluble (e.g. suspension) non-antigen bioactive agent can be present in the composition unencapsulated.

Furthermore, in methods using these compositions, the non-antigen bioactive agent can be administered to the subject in an administration of a composition of this invention separate from the administration of an encapsulated antigen, wherein the antigen is administered in a composition of this invention or in another composition. The administration of the non-antigen bioactive agent composition of this invention can be prior to, simultaneously with, or after administration of the antigen.

The present invention also provides compositions for potentiating an immune response to an antigen. Thus, specifically, provided is a composition for potentiating a preexisting CTL response to an antigen in a subject, comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated CTL response is measurable within fourteen days of a single administration at a level greater than the preexisting CTL response.

Further provided is a composition for potentiating a preexisting T helper cell response to an antigen in a subject, comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated T helper cell response is measurable within fourteen days of a single administration at a level greater than the preexisting T helper cell response.

Additionally provided is a composition for potentiating a preexisting neutralizing antibody response to an antigen in a subject, comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within fourteen days of a second or subsequent administration at a level greater than the preexisting neutralizing antibody response.

Further provided is a composition for potentiating a neutralizing antibody response to an antigen in a subject, comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within thirty days of a single administration at a level greater than the preexisting neutralizing antibody response.

The invention further relates to a composition for inducing a CTL, T helper or neutralizing antibody response in a subject, comprising an effective amount of a composition comprising an antigen or a nucleic acid encoding the antigen, encapsulated in a polymeric composition, wherein the polymeric composition comprises a biodegradable polymer with a molecular weight of less than or equal to 7000 daltons.

The invention further relates to a composition for inducing a CTL, T helper or neutralizing antibody response in a subject, comprising an effective amount of a composition comprising an antigen or a nucleic acid encoding the antigen, encapsulated in a polymeric composition, wherein the polymeric composition comprises a biodegradable polymer with an inherent viscosity of less than 0.4 dL/g.

The invention further relates to a composition for inducing a CTL, T helper cell or neutralizing antibody response in a subject, comprising an effective amount of a composition comprising an antigen or nucleic acid encoding the antigen, encapsulated in a polymeric composition, wherein the polymeric composition comprises an unblocked polymer of poly(lactide-co-glycolide), polylactide or polyglycolide.

The invention further relates to a composition for potentiating a CTL, T helper or neutralizing antibody response in a subject, comprising an effective amount of a composition comprising a bioactive agent encapsulated in a polymeric composition, wherein the polymeric composition comprises a biodegradable polymer with a molecular weight of less than or equal to 7000 daltons.

The invention further relates to a composition for potentiating a CTL, T helper or neutralizing antibody response in a subject, comprising an effective amount of a composition comprising a bioactive agent encapsulated in a polymeric composition, wherein the polymeric composition comprises a biodegradable polymer with an inherent viscosity of less than 0.4 dL/g.

The invention further relates to a composition for potentiating a CTL, T helper cell or neutralizing antibody response in a subject, comprising an effective amount of a composition comprising a bioactive agent encapsulated in a polymeric composition, wherein the polymeric composition comprises an unblocked polymer of poly(lactide-co-glycolide), polylactide or polyglycolide.

In any composition of this invention used for inducing or potentiating an immune response, the bioactive agent is an agent capable of inducing or potentiating an immune response upon administration to a subject. In a preferred embodiment, the immune response that is induced or potentiated is a CTL, T helper cell or neutralizing antibody response. Thus, the bioactive agent can comprise an antigen to which the immune response is induced or potentiated, or the bioactive agent can comprise a nucleic acid functionally encoding such an antigen. Alternatively, the bioactive agent can comprise an adjuvant or immunomodulator, as further described and illustrated below. A nucleic acid functionally encoding an antigen is a nucleic acid capable of expression of the antigen in the cells into which the nucleic acid will be uptaken; for example, such a nucleic acid will have appropriate expression controls (e.g., promoter, enhancer, if desired, translation start codon, polyadenylation signal etc.) and codon usage compatible with the cells.

Compositions of this invention can produce a combination of immune responses in the subject to whom the compositions are administered. Thus, one can achieve one or more of, for example, a cytotoxic T cell (CTL) response, a T helper response, and a neutralizing antibody response. Each response can be measured or detected according to standard methods known in the art and as taught herein. A neutralizing antibody response, for example, can be determined after a first, often priming, administration or after a second, or boost, administration.

In a preferred embodiment, all compositions of this invention (both single and blend component systems), for a CTL response, the response can be measured by the percentage of cytotoxicity achieved, which is a method standard in the art, and which is taught herein. For a CTL response, a satisfactory composition is one that is capable of kinetics of bioactive agent release, e.g., antigen or nucleic acid release, such that preferably a CTL response measurable or detectable within fourteen to 30 days of a single administration at a level of at least 30% cytotoxicity is achieved. Such level can be higher, such as 40% cytotoxicity, 50% cytotoxicity, 60% cytotoxicity, 70% cytotoxicity, 80% cytotoxicity, 90% cytotoxicity or even 100% cytotoxicity. The phrase "kinetics of release" is defined as the rate the bioactive agent is released from the encapsulated polymeric composition. Additionally, the response may be detectable at a selected level of cytotoxicity within shorter periods of time, such as at twelve days, ten days, eight days, seven days, five days or sooner, after a single administration of the composition. In a preferred embodiment, the response can be measured or detected at a selected level of cytotoxicity at seven days.

In a preferred embodiment, all compositions of this invention (both single and blend component systems), for a T helper cell response, the response can be measured by T cell proliferation or cytokine induction, which are methods standard in the art, and which are also taught herein. For a T helper cell response, a satisfactory composition is one that is preferably capable of kinetics of bioactive agent release, e.g., antigen or nucleic acid release, such that a T helper cell response is measurable, or detectable, within fourteen days of a single administration of the composition at a level of at least two-fold over background, as measured by T cell proliferation or cytokine induction. A stronger response can also be obtained, such as three-fold, four-fold, five-fold, ten-fold, twenty-five fold, fifty-fold, a hundred-fold or higher over background. Additionally, a faster response may be achieved, such as a level of at least two-fold over background within twelve days, ten days, eight days, seven days, five days or sooner, after a single administration of the composition. In a preferred embodiment, the response can be measured or detected at a selected level of T cell proliferation at seven days.

In a preferred embodiment, all compositions of this invention (both single and blend component systems), a neutralizing antibody response comprises the inactivation of a microbial product, such as a toxin by an antibody or counteraction of a microorganism's infectivity, especially the neutralization of viruses (see, e.g. Illustrated Dictionary of Immunology; Cruse and Lewis, CRC press; 1994; Peyer's patch 217). For a neutralizing antibody response, a satisfactory composition is one that preferably provides kinetics of bioactive agent release, e.g., antigen or nucleic acid release, such that minimally, from a first administration, one can achieve measurable, or detectable, antibody levels of significance (i.e., at least two-fold over background) within fourteen days upon a second, or boost, administration of the antigen, whether the second administration is of the present composition or of the antigen in another composition not of this invention. Additionally, a satisfactory composition is one that is capable preferably of kinetics of bioactive agent release, e.g., antigen or nucleic acid release, such that one can achieve measurable, or detectable antibody levels of significance (i.e., at least two-fold over background) within thirty days of a single administration. The level of neutralizing antibody is at least two-fold over background, but can also be, for example, three-fold, four-fold, five-fold, ten-fold, twenty-five fold, fifty-fold, a hundred-fold or higher over background. In one embodiment, the response can be measured or detected at a selected level of antibody titer at twenty-one days. In another embodiment, the response can be measured or detected at a selected level of antibody titer at ten days.

In a preferred embodiment, all compositions of this invention (both single and blend component systems) can be used as a second, or boost administration and/or as a potentiator of an earlier CTL response. A satisfactory composition for this use is one that is capable of kinetics of release of a bioactive agent, such that preferably a potentiated CTL response is measurable or detectable within fourteen days of a single administration at a level greater than the preexisting CTL response. Such a level can preferably be at least 30% cytotoxicity, 40% cytotoxicity, 50% cytotoxicity, 60% cytotoxicity, 70% cytotoxicity, 80% cytotoxicity, 90% cytotoxicity or even 100% cytotoxicity. Additionally, the response may be detectable at a selected level of cytotoxicity such as a level greater than the preexisting CTL response within shorter periods of time, such as at twelve days, ten days, eight days, seven days, five days or sooner, after a single administration of the composition. In a preferred embodiment, the potentiated response can be measured or detected within seven days of a single administration at a level greater than the preexisting CTL response.

In a preferred embodiment, all compositions of this invention (both single and blend component systems) can be used as a second, or boost administration and/or as a potentiator of an earlier T helper cell response. The response can be measured by T cell proliferation or cytokine induction, which are methods standard in the art, and which are also taught herein. For a T helper cell response, a satisfactory composition for this potentiating use is one that is preferably capable of kinetics of bioactive agent release, such that a potentiated T helper cell response is measurable, or detectable, within fourteen days of a single administration of the composition at a level greater than the preexisting T helper cell response or at least two-fold over background, as measured by T cell proliferation or cytokine induction. A stronger response can also be obtained, such as at least three-fold, four-fold, five-fold, ten-fold, twenty-five fold, fifty-fold, a hundred-fold or higher over background. Additionally, a faster response may be achieved, such as a level greater than the preexisting T helper cell response or at least two-fold over background within twelve days, ten days, eight days, seven days, five days or sooner, after a single administration of the composition. In a preferred embodiment, the response can be measured or detected at a selected level of T cell proliferation at seven days such as at a level greater than the preexisting T helper cell response.

Additionally, all compositions of the present invention can be utilized as a second, or boost administration and/or as a potentiator of an earlier neutralizing antibody response. For such a use, a composition of this invention will preferably achieve measurable or detectable antibody levels of significance (e.g. greater than the preexisting neutralizing antibody response or at least two-fold over background) within fourteen days or in other embodiments within twelve days, ten days, eight days, seven days, five days, or sooner, upon a second, or boost, administration of the bioactive agent (e.g. antigen), whether the second administration is of the present composition or of the bioactive agent in another composition not of this invention. Additionally, a satisfactory composition is one that is preferably capable of kinetics of bioactive agent release such that one can achieve measurable, or detectable antibody levels of significance (e.g. greater than the preexisting neutralizing antibody response or at least two-fold over background) within thirty days of a single administration or in other embodiments within 25 days, 21 days, 18 days, 15 days, or sooner. The level of neutralizing antibody is preferably at least two-fold over background, but can also be, for example, at least three-fold, four-fold, five-fold, ten-fold, twenty-five fold, fifty-fold, a hundred-fold or higher over background.

In the compositions of this invention, the component(s) of the polymeric composition are preferably biocompatible, which term is known in the art to include that the components are substantially non-toxic, non carcinogenic, and should not substantially induce inflammation in body tissues upon administration.

The term "blend" with respect to the polymeric composition is defined as the combination of two or more polymeric components to form one overall polymeric composition that microencapsulates a bioactive agent. As used herein, when referring to the polymeric compositions, the term "blend" is different from the term "mixture." A "mixture" is defined herein as a combination of microencapsulated structures each of separate types of compositions to produce a combination of separate, excipient types of encapsulated bioactive agents. Thus a blend is two or more components which are first combined together to then form a single either uniform or non-uniform composition excipient material whereas a mixture first forms at least two different microencapsulated structures from separate components and then combines the separate microencapsulated structures together. So for a mixture, a first microencapsulated structure is made and then a second microencapsulated structure is made different from the first, and then the first and second microencapsulated structures are combined in one composition.

In one embodiment, the polymeric composition used to encapsulate the bioactive agent comprises a polymeric blend component system. The term "blend component system" is defined herein as an encapsulated system, wherein the polymeric composition or blend used to encapsulate the bioactive agent comprises at least two components.

The first component of the blend component system, which is referred to herein as component (a), is a polymer present in an amount sufficient to provide structural integrity to the polymeric composition. At a minimum, because component (b) is typically a liquid, a near liquid, or tacky at room temperature, component (a) must impart stability to provide a solid or non-tacky structure in combination with component (b) at room temperature. The amount of component (a) can be just enough to provide minimum integrity to the polymer composition or more than that minimum amount. As the amount of component (a) is added in excess of what is needed for structural integrity, the rapidity of release of the bioactive agent decreases. Component (a) stabilizes the composition, which typically results in the formation and isolation of a stable powder. The present invention is preferably a stable powder, which is easy to store and handle.

Moreover, because the polymeric composition used to encapsulate the bioactive agent of the present invention preferably results in a stable powder, the resultant composition is preferably not tacky and does not become tacky or aggregate once it is added to a liquid vehicle. Typically, when a liquid or gel composition is added to a liquid vehicle, the polymeric composition will not disperse evenly in the liquid vehicle, which results in an uneven concentration of the encapsulated bioactive agent in the liquid vehicle. This is not the case with the present invention, which preferably utilizes an encapsulated bioactive agent in the form of a powder. Once added to a liquid vehicle, the encapsulated bioactive agent preferably disperses evenly throughout the solution, which results in the formation of a uniform dispersion.

The phrase "amount sufficient to provide structural integrity" is defined as the amount of component (a) required for the encapsulated bioactive agent to retain its original shape and bioactive agent retention characteristics in a dispersion, such that the bioactive agent is released at a designated time after administration of the encapsulated bioactive agent in a liquid vehicle. Moreover, "amount sufficient to provide structural integrity" is further defined as the amount of component (a) required to maintain the encapsulated bioactive agent as individual particles when stored. The sufficient amount can be just enough to provide this minimum integrity or more than that minimum amount.

The second component of the polymeric composition, which is referred to herein as component (b), provides for the rapid release of the bioactive agent. Component (b) can be but is not limited to 1) a rapidly biodegradable component, 2) a rapidly dissolving component, 3) a component that causes osmotic rupture of the encapsulated polymeric composition or 4) a component that causes the encapsulated polymeric composition to swell and form a gel-like structure. Component (b) can be a single component that has one or any combination of more than one property described above (i.e. rapidly biodegradable, rapidly dissolving, rapidly swelling or osmotic rupture property). Component (b) can be, for example, a rapidly biodegradable component, but also can have any of the other three properties, depending upon the composition of component (b). Thus, component (b) can have any single or combination of the four features described above. Component (b) can also comprise a mixture of two or more different type components described above. The terms "rapidly biodegradable" and "rapidly dissolving" when describing component (b) of the present invention are defined herein such that component (b) will, at a minimum, biodegrade or dissolve at a higher rate than component (a). Components (a) and (b) can biodegrade by a number of methods, which include but are not limited to hydrolysis or enzymatic degradation. The rate component (b) biodegrades or dissolves relative to component (a) depends upon the materials selected for components (a) and (b). More specifically, the term "rapidly" indicates that component (b) biodegrades or dissolves or swells at a rate so as to enable the release of the bioactive agent within a period of time for inducing or potentiating a CTL response, a T helper response and a neutralizing antibody response. Such a response can occur within a couple of hours to more than four hours, more than six hours, more than 24, 36, 48 and up to two weeks to at least a month after administration.

In one embodiment, the rate that component (b) biodegrades or dissolves or swells relative to the component (a) is one and a half times as fast as component (a). For example, component (b) biodegrades or dissolves or swells relative to the component (a) can be twice as fast, five times as fast, ten times as fast, and so forth wherein a measureable CTL response, T helper response, or neutralizing antibody response is observed.

Component (b) may also permit the release of the encapsulated bioactive agent via osmotic rupture. Once the encapsulated bioactive agent is administered, the body fluids can permeate the polymeric composition through component (b), which results in the swelling and rupture of the encapsulated bioactive agent with concurrent release of the bioactive agent. The encapsulated polymeric composition can also absorb water, which results in the conversion of the encapsulated polymeric composition into a rapidly swelling gel-like structure. The bioactive agent can then leach out of the polymeric composition.

Materials that are useful for component (b) include but are not limited to an acidic salt, a basic salt, a neutral salt, a carbohydrate, a starch, a polyelectrolyte, biocompatible hydrophilic materials, swellable materials, a gelatin, an amine, a surfactant, an inorganic acid or base, an organic acid or base, an amino acid, a monomer, an oligomer, a polymer or a mixture thereof. In one embodiment, component (b) can include but is not limited to sodium chloride, sodium phosphate, bile salts, ammonium sulfate, ammonium chloride, sodium carbonate or potassium carbonate, polyethylene glycol, polyoxoethylene alkyl ethers, trehalose, mannitol, sorbitol, dextrose, dextrin, sucrose, lactose, saccharides, polysaccharides, oligosaccharides, saccharin, carboxymethyl cellulose, hydroxypropyl cellulose, hydroxypropyl methyl cellulose, methyl cellulose or sodium starch glycolate, citric acid, lactic acid, glycolic acid, acetic acid, ascorbic acid, tartaric acid, malic acid, maleic acid, benzoic acid, arginine, glycine, threonine, choline, ethanolamine, protamine, sodium alginate, heparin, docusate sodium, glycerin, glycofurol, propylene glycol, polysorbate, povidone, and albumin.

In one embodiment, component (b) increases the biodegradability of component (a) via hydrolysis. Examples of component (b) include but are not limited to acids, bases, acidic or basic salts, organic acids, monomers and polymers. In a preferred embodiment, sodium chloride, sodium phosphate, bile salts, ammonium sulfate, ammonium chloride, sodium carbonate, potassium carbonate, citric acid, lactic acid, glycolic acid, acetic acid, ascorbic acid, tartaric acid, malic acid, maleic acid or benzoic acid can be used.

In another embodiment, component (b) increases the rate of release of the bioactive agent by increasing the porosity of the encapsulated bioactive agent via rapidly dissolution of component (b). Examples of component (b) include but are not limited to neutral salts, acidic salts, basic salts, carbohydrates, starch, amino acids, low-molecular weight polyethylene glycol, propylene glycol, polysorbates or povidone. In a preferred embodiment, sodium chloride, sodium phosphate, bile salts, ammonium sulfate, ammonium chloride, sodium carbonate or potassium carbonate, trehalose, mannitol, sorbitol, dextrose, dextrin, sucrose, lactose, saccharides, polysaccharides, oligosaccharides, saccharin, carboxymethyl cellulose, hydroxypropyl cellulose, hydroxypropyl methyl cellulose, methyl cellulose or sodium starch glycolate, arginine, glycine or threonine can be used.

In another embodiment, component (b) increases the rate of release of the bioactive agent by drawing water into the encapsulated bioactive agent resulting in increased osmotic pressure and/or swelling of the encapsulated bioactive agent. Examples of swellable materials include but are not limited to polysaccharides, starches and carbohydrates. In a preferred embodiment, the swellable material can be carboxymethyl cellulose, hydroxypropyl cellulose, hydroxypropyl methyl cellulose, methyl cellulose, high-molecular weight polyethylene glycol, high-molecular weight propylene glycol, gelatin, docusate, sodium alginate, sodium starch glycolate, sorbitol and high molecular weight sugars.

A wide variety polymers can be used for components (a) and/or (b). In one embodiment, component (a) and/or (b) can be a poly(diene), a poly(alkene), a poly(acrylic), a poly(methacrylic), a poly(vinyl ether), a poly(vinyl alcohol), a poly(vinyl ketone), a poly(vinyl halide), a poly(vinyl nitrile), a poly(vinyl ester), a poly(styrene), a poly(carbonate), a poly(ester), a poly(orthoester), a poly(esteramide), a poly(anhydride), a poly(urethane), a poly(amide), a cellulose ether, a cellulose ester, a poly(saccharide), poly(lactide-co-glycolide), a poly(lactide), a poly(glycolide), a copolyoxalate, a polycaprolactone, a poly(lactide-co-caprolactone), a poly(esteramide), a polyorthoester, a poly(a-hydroxybutyric acid), a polyanhydride or a mixture thereof. In a preferred embodiment, components (a) and (b) comprise a poly(lactide-co-glycolide), a poly(lactide), a poly(glycolide), a copolyoxalate, a polycaprolactone, a poly(lactide-co-caprolactone), a poly(esteramide), a polyorthoester, a poly(a-hydroxybutyric acid), a polyanhydride, or a mixture thereof.

Components (a) and/or (b) can also be polymers derived from the polymerization of at least one monomer. In another embodiment, component (b) can be a polymer or oligomer derived from the polymerization or oligomerization of at least one monomer. Examples of suitable monomers include an alpha hydroxycarboxylic acid, a lactone, a diene, an alkene, an acrylate, a methacrylate, a vinyl ether, a vinyl alcohol, a vinyl ketone, a vinyl halide, a vinyl nitrile, a vinyl ester, styrene, a carbonate, an ester, an orthoester, an esteramide, an anhydride, a urethane, an amide, a cellulose ether, a cellulose ester, a saccharide, an alpha hydroxycarboxylic acid, a lactone, an esteramide or a mixture thereof. In another embodiment, the monomers listed above can also be used for component (b).

In a preferred embodiment, component (a) and/or (b) is the polymerization product of an alpha hydroxycarboxylic acid, a lactone or a mixture thereof. In an even more preferred embodiment, the alpha hydroxycarboxylic acid comprises glycolic acid, lactic acid, a-hydroxy butyric acid, a-hydroxyisobutyric acid, a-hydroxyvaleric acid, a-hydroxyisovaleric acid, a-hydroxy caproic acid, a-hydroxy-a-ethylbutyric acid, a-hydroxyisocaproic acid, a-hydroxy-3-methylvaleric acid, a-hydroxyheptanoic acid, a-hydroxyoctanoic acid, a-hydroxydecanoic acid, a-hydroxymysristic acid, a-hydroxystearic acid, a-hydroxyligoceric acid or a mixture thereof. In one embodiment, the lactone comprises 3-propiolactone, tetramethyleneglycolide, b-butyrolactone, 4-butyrolactone, pivalactone or mixtures thereof.

In another embodiment, component (a) and/or (b) comprises the co-polymerization product of a glycolide, lactide or a mixture thereof. In the case of lactide, the D-, L- and DL- forms are useful in the present invention. In a one embodiment, component (a) comprises a polymer formed from components comprising 40 to 100 mole % lactide and from 0 to 60 mole % glycolide. In a preferred embodiment, component (b) comprises a polymer formed from components comprising 0 to 100 mole % lactide and from 0 to 100 mole % glycolide. In another embodiment, components (a) and (b) can both be a copolymer comprising the polymerization of lactide and glycolide. In a preferred embodiment, component (a) is a copolymer of glycolide and lactide and component (b) is a homopolymer of lactide. In an even more preferred embodiment, component (a) is from 60:40 to 50:50 poly(lactide-co-glycolide) and (b) is poly(lactide).

When components (a) and/or (b) are polymers, oligomers or monomers that possess a terminal carboxylic acid moiety, they are referred to herein as unblocked. When the end group is not a carboxylic acid, for example, an ester, then the resultant polymer, oligomer or monomer is referred to as blocked. The unblocked polymer, oligomer or monomer adsorb more water and hydrolytically degrade faster due to the presence of the carboxyl group in comparison to the blocked analogs. In the present invention, component (a) and/or (b) can be blocked or unblocked. In one embodiment, components (a) and/or (b) are blocked in the blend component system.

The amount of components (a) and (b) in the blend component system of the present invention may vary. In one embodiment, component (a) is from 5 to 95 wt % and component (b) is from 95 to 5 wt % of the polymeric composition weight. In another embodiment, the amount of component (a) is greater than the amount of component (b). In a preferred embodiment, component (a) is from 50 to 90 wt % and component (b) is from 10 to 50 wt % of the polymeric composition weight. In another embodiment, the amount of component (a) is less than the amount of component (b). In this embodiment, component (a) is from 10 to 50 wt % and component (b) is from 50 to 90 wt % of the polymeric composition weight. In another embodiment, the polymeric composition blend component system consists essentially of components (a) and (b).

The molecular weight of components (a) and/or (b) may also vary. The molecular weight of component (a) can be less than, greater than, or equal to component (b) when component (b) is a polymer. In a preferred embodiment, the molecular weight of component (a) is greater than the molecular weight of (b). The molecular weight of the polymer can also be related to inherent viscosity. The higher the value for the inherent viscosity, the greater the molecular weight of the polymer. In one embodiment, component (a) has an inherent viscosity of less than 4.0 dL/g and component (b) has an inherent viscosity of less than 2.0 dL/g and is less than the inherent viscosity of component (a). When measuring the inherent viscosity of a polymer, the composition of the polymer and the solubility of the polymer should be considered. The selection of the appropriate solvent and the determination of the inherent viscosity of polymers is known in the art. In one embodiment, chloroform and hexafluoroisopropanol are useful solvents in determining the inherent viscosity of a polymer. In another embodiment, if the lactide content is less than 65 mole % or a homopolymer of polyglycolide, the solvent used can be hexafluoroisopropanol. In another embodiment, when the lactide content of a lactide-glycolide polymer is greater than 65 mole % or a homopolymer of polylactide, the solvent used can be chloroform. In another embodiment, component (a) has an inherent viscosity of from 0.4, 0.6, 0.8, 1.0, 1.5, 2.0, 2.5 or 3.0 dL/g to 0.5, 1.0, 2.0, 3.0, 3.5, or 4.0 dL/g and component (b) has an inherent viscosity of from 0.01 to 2.0 dL/g, preferably from 0.01 to 0.5 dL/g, and even more preferably from 0.01 to 0.25 dL/g. In a preferred embodiment, component (a) is 60:40 mole % poly(lactide-co-glycolide) with an inherent viscosity of 0.49 dL/g in chloroform or 50:50 poly(lactide-co-glycolide) with an inherent viscosity of 0.39 dL/g in hexafluoroisopropanol and component (b) is poly(lactide) with a molecular weight of from 2000 daltons to 7000 daltons. Molecular weight measurements or determinations of the components are known or readily ascertainable by standard methods, and the components (a) and (b) for any desired composition are selected accordingly to achieve structural integrity by component (a) and rapid release of the bioactive agent by component (b).

"Bioactive agent" as used in the present invention is a biocompatible agent capable of inducing or potentiating an immune response upon administration to a subject, such as an antigen, adjuvant or immunomodulator, as further described and illustrated below, or a nucleic acid functionally encoding such a bioactive agent. By "inducing" an immune response is meant that, upon administration of an antigen or a nucleic acid encoding the antigen, encapsulated in the composition, an immune response is effected, that is, is stimulated, initiated or induced. The present method can also be used to enhance an induction of immune response over that achieved by immunization with the antigen alone or in another immunological preparation that does not rapidly release as the present invention does. By "potentiating" an immune response is meant that, upon administration of an antigen or another bioactive agent encapsulated in the composition, a preexisting immune response is improved, furthered, supplemented, amplified, increased or prolonged. The present method can also be used to enhance a potentiation of immune response over that achieved by immunization with the bioactive agent alone or in another immunological preparation that does not rapidly release as the present invention does.

One can determine a resulting immune response by any of several methods, including detecting the presence of antibodies specific for the antigen, determining T-cell proliferative response, determining a cytotoxic T-cell response, among other detection means known in the art. Such methods are known in the art and described herein. By "immune response" is meant any response of the immune system, including but not limited to cellular as well as local and systemic humoral immunity, such as CTL responses, including antigen-specific induction of CD8+ CTLs, helper T-cell responses including T-cell proliferative responses and cytokine release, and B-cell responses including antibody response.

Thus, the present compositions can be utilized for MHC class I and MHC class II responses. The present invention, however, is particularly noted for its ability to induce or potentiate MHC class 1-mediated responses. The more rapid the release of the bioactive agent, whether antigen or another bioactive agent, the more potentially rapid the immune response and thus the stronger the overall immune response that becomes possible. Typically, the CTL response is induced or potentiated by the present compositions, in addition to inducement or potentiation of B-cell response, including production of antibodies, and T helper cell responses.

The present method advantageously provides methods that promote rapid release of the bioactive agent from the composition, thus providing a method of introducing the bioactive agent into the phagocytic pathways and eliciting MHC class I-mediated responses in addition to MHC class II-mediated immune responses. Bioactive agents useful in the present invention include but are not limited to an adjuvant (e.g., adjuvants listed in Vaccine Design, The Subunit and Adjuvant Approach (Powell, M. F. and M. J. Newman, eds.) Pharmaceutical Biotechnology Volume 6, Plenum Press (New York 1995); an antigen; a nucleic acid functionally encoding an antigen; an immunomodulator; a compound or collection of compounds capable of eliciting a Th1-type cytokine response (such as LeIF); a molecule capable of interacting with and/or upregulating co-stimulatory molecules on T-cells (such as anti-CD28 antibodies); or a mixture thereof.

When the bioactive agent is an antigen, in one embodiment, the antigen can comprise a peptide, polypeptide, or protein. Examples of an antigen include but are not limited to an allergen, a viral antigen, a bacterial antigen such as a bacterial DNA, a protozoan antigen, a tumor antigen, a fungal antigen; an infectious disease antigen or a mixture thereof. Specifically, for example, a tumor antigen can be Her-2/neu protein, protein fragments or peptides, PSA, PSM, mammaglobin, prolactin inducing protein (PIP), p21 or p53; an infectious disease antigen can be hepatitis B surface antigens, hepatitis C antigens, malaria antigens, TB antigens, chlamydia antigens, Herpes antigens, flu antigens, HIV antigens, EBV antigens, papilloma antigens and H. pylori antigens. Antigens, including antigenic fragments of a protein, can readily be determined by standard means of determining antigenicity of substances.

As stated above, the bioactive agent of the present invention can be an adjuvant. As known in the art, an adjuvant is a substance which, when in the context of an antigen, enhances the immune response of the antigen. In general, adjuvants can include such molecules as cytokines, immunomodulators, and co-stimulatory molecules. For in vivo use, non-toxic adjuvants should be selected, as known in the art. An adjuvant can be selected by standard criteria based on the antigen used, the mode of administration and the subject (Arnon, R. (Ed.) Synthetic Vaccines 1:83–92, CRC Press, Inc., Boca Raton, Fla., 1987). With the use of an adjuvant, it is possible to induce or potentiate an even stronger immune response when used in combination with another bioactive agent. For example, the polymeric composition can contain another bioactive agent and an adjuvant, wherein an adjuvant is encapsulated in a second polymeric composition, where in the second polymeric composition comprises a blend of a polymer present in an amount sufficient to provide structural integrity to the polymeric composition and a rapidly biodegradable component, a rapdily dissolving component, a rapidly swelling component, or a component that causes osmotic rupture of the encapsulated polymeric composition.

A bioactive agent can also comprise a nucleic acid functionally encoding an adjuvant.

Useful adjuvants include but are not limited to a cytokine, such as a lymphokine, a monokine or a chemokine, or a cytokine inducer or an agent that facilitates the entry of the encapsulated bioactive agent into the cytoplasm of the cell. In one embodiment, the cytokine comprises IL-1, IL-2, IL-6, IL-12, IL-15, IL-18, IFN-ã, IFN-á, GM-CSF, Flt31, or a mixture thereof. These cytokines could be administered either as soluble or non-soluble entities with an encapsulated antigen or encapsulated in microsphere formulations.

Other examples of adjuvants that are useful in the present invention include but are not limited to plasmid DNA or bacterial agents. An adjuvant can also include, for example, an immunomodulator. An immunomodulator could upregulate co-stimulatory molecules such as B7 or CTLA-4 or it could enhance Th1 type responses. Molecules which enhance a Th1 type response in vivo could be administered with antigen containing microspheres to enhance T-cell responses preferentially. An example of such a molecule is LeIF, a leishmania derived protein that has been shown to induce a Th1 response. Furthermore, a nucleic acid encoding a co-stimulatory molecule can be administered to provide the co-stimulatory molecule.

Additional adjuvants include any compound described in Chapter 7 (pp 141–227) of "Vaccine Design, The Subunit and Adjuvant Approach" (eds. Powell, M. F. and Newman, M. J.) Pharmaceutical Biotechnology, Volume 6, Plenum Press (New York), Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the encapsulated bioactive agent in the cytoplasm of a cell such as listeriolysin, streptolysin or a mixture thereof.

In one embodiment, the bioactive agent can comprise, for example, a lipid; a nucleic acid; a peptide, polypeptide, or protein.

In an embodiment of the invention, the composition comprises an antigen, or nucleic acid functionally encoding the antigen, encapsulated in the polymeric composition. In another embodiment of the invention, the composition comprises an antigen, or nucleic acid functionally encoding the antigen, and an adjuvant encapsulated in the polymeric composition. In this embodiment, the antigen and adjuvant can be encapsulated within the same microsphere or they can be encapsulated separately but administered together in one composition. In the case when the antigen and adjuvant are encapsulated separately, they can be encapsulated using the identical polymeric composition or different polymeric composition. In another embodiment, the composition comprises an antigen, or nucleic acid functionally encoding the antigen, encapsulated in the polymeric composition, and an adjuvant present in the composition unencapsulated, i.e., as a free (e.g. soluble or non-soluble emulsion) adjuvant. In another embodiment, the composition comprises an adjuvant, encapsulated in the polymeric composition, which composition can be administered to induce or potentiate an immune response to an antigen previously administered or administered after the composition, wherein the antigen is administered either by encapsulation according to this invention or by another method.

In yet another embodiment, the composition comprises an adjuvant encapsulated in the polymeric composition, and an antigen present in the composition unencapsulated, i.e., as soluble or non-soluble antigen. In such an embodiment, the encapsulated adjuvant can enhance the immune response to the antigen. In another embodiment, the composition comprises an adjuvant encapsulated in a small particle, for example, less than or equal to 10 im. In yet another embodiment, the composition comprises an adjuvant encapsulated in a large particle, for example greater than 10 im.

Immune response-inducing or -potentiating amounts of an antigen can be determined using standard procedures. Briefly, various concentrations of a specific immunoreactive epitope are prepared, encapsulated in the composition and administered to an animal and the immunological response (e.g., the production of antibodies or cell mediated immunity), or the increase (magnitude or time length) in response, of an animal to each concentration is determined. Immune response-inducing or -potentiating amounts of any other bioactive agent can be determined in similar fashion using standard procedures, wherein various concentrations of the bioactive agent are prepared, encapsulated, and administered in conditions such that immunological response to an antigen (already present or administered before, simultaneously with or after the present bioactive agent) can be determined. The amounts of antigen or other bioactive agent administered can depend on the subject, e.g. a human or a guinea pig, the condition of the subject, the size of the subject, etc. These immune response-inducing or -potentiating amounts can be extrapolated by relative body weight to human or other subjects. For vaccine uses, thereafter an animal so inoculated with an antigen can be exposed to the antigen to test the vaccine effect of the specific composition administered.

As used herein, "an effective amount" of a composition is that amount capable of achieving the desired effect. The effective amount is an effective amount within each encapsulated structure that is sufficient to produce the desired response. As described above, an effective amount can be an amount sufficient to prime, induce or potentiate an immune response. An effective amount can also be an amount sufficient to induce or potentiate a T-cell response, an amount sufficient to induce or potentiate an antibody response (i.e., antibody production), an amount sufficient to induce or potentiate a cytotoxic T-cell response, an amount sufficient to induce or potentiate activation of CD8-positive T lymphocytes specific for an antigen, an amount sufficient to induce or potentiate activation of CD4-positive T lymphocytes specific for an antigen, depending upon the context in which it is used. Such amounts can readily be determined for any specific composition using standard methods and as described herein.

It can be appreciated from the teachings herein that the composition can be used as a prophylactic or a therapeutic modality.

The amount of bioactive agent that is encapsulated by the polymeric composition varies depending upon the bioactive agent employed. When the bioactive agent is an antigen, it can be present in an immune response inducing or potentiating amount. In one embodiment, the bioactive agent is less than 80% by weight of the total composition. In a preferred embodiment, the bioactive agent is from 0.01 to 10% by weight of the total composition. In one embodiment, the amount of bioactive agent, such as antigen or a nucleic acid encoding the antigen is 1 ng to 10 mg per injection/individual. In another embodiment, the bioactive agent is from 1 ng to 500 µg per injection/individual. In another embodiment, the amount of bioactive agent is 100 mg per injection/individual. In a preferred embodiment, the amount of antigen is from 1 ig to 5 mg per injection/individual.

The invention further relates to a composition for inducing or potentiating an immune response in a subject, comprising a bioactive agent capable of inducing or potentiating an immune response encapsulated in a polymeric composition, wherein the polymeric composition comprises a biodegradable polymer with an inherent viscosity of less than 0.4 dL/g. When the composition is to be used for inducing an immune response, the bioactive agent is preferably an antigen. When the composition is to be used for potentiating an immune response, the bioactive agent is preferably an antigen or other bioactive agent as defined herein.

The invention further relates to a composition for inducing or potentiating a CTL, T helper cell or neutralizing antibody response in a subject, comprising a bioactive agent capable of inducing or potentiating a CTL, T helper cell or neutralizing antibody response encapsulated in a polymeric composition, wherein the polymeric composition comprises a biodegradable polymer with a molecular weight of less than or equal to 7000 daltons. When the composition is to be used for inducing a CTL, T helper cell or neutralizing antibody response, the bioactive agent is preferably an antigen. When the composition is to be used for potentiating a CTL, T helper cell or neutralizing antibody response, the bioactive agent is preferably an antigen or other bioactive agent as defined herein.

The invention further relates to a composition for inducing or potentiating a CTL, T helper cell or neutralizing antibody response in a subject, comprising an antigen capable of inducing or potentiating a CTL, T helper cell or neutralizing antibody response encapsulated in a polymeric composition, wherein the polymeric composition comprises an unblocked polymer of poly(lactide-co-glycolide), polylactide or polyglycolide. When the composition is to be used for inducing a CTL, T helper cell or neutralizing antibody response, the bioactive agent will be an antigen. When the composition is to be used for potentiating a CTL, T helper cell or neutralizing antibody response, the bioactive agent can be an antigen or other bioactive agent as defined herein.

This composition, which will be referred to herein as a single component system, is similar to the blend component system with the exception that component (b) is not present in the single polymeric composition. However, the single component typically is of a composition that biodegrades faster than component (a) of the blend system, while still maintaining its solid structural integrity and encapsulation of the bioactive agent prior to administration and preferably, prior to phagocytosis. The single component system biodegrades more rapidly than other single compositions of the prior art. The blend system of the invention will typically perform better, i.e. more rapidly release the bioactive agent, than the single component system. This is because component (b) of the blend system can be stabilized by component (a) yet component (b) causes very rapid release. Nevertheless, the single component system is still useful for the rapid release aspect and is an improvement over single component prior art systems. The bioactive agents, including adjuvants and antigens, and polymers used in component (a) of the blend component system as described above are useful for the single component system. The single component system thus utilizes the same type excipients or polymers used to encapsulate the bioactive agent as in the blend system, except the single system, to achieve rapid release without the presence and benefit of component (b) of the blend system, typically uses a more rapidly releasing polymer than component (a) of the blend system. This is achieved by using, for example, a lower molecular weight or lower inherent viscosity polymer than the typical component (a) polymer or an unblocked polymer.

In one embodiment, the molecular weight of the biodegradable polymer in the single component system is preferably less than 7000 daltons, more preferably from 2000 to 7000 daltons, more preferably from 2000 to 6000 daltons, and even more preferably from 2000 to 5000 daltons. The molecular weight should be high enough for the polymer to be in the solid form. Similar to one embodiment of component (a) of the blend component system, the polymer composition of the single component system biodegrades by hydrolysis or enzymatic degradation, preferably by hydrolysis.

The composition of the single and blend component invention rapidly releases the bioactive agent. By "rapidly release" as used herein is meant rapidly releasing the bioactive agent quickly upon uptake into a cell. Rapid release upon uptake into the cell can induce an MHC class I-mediated response. Thus, the present compositions advantageously provide rapid release of the bioactive agent upon administration and are capable of inducing an immune response and in particular a CTL response.

In one embodiment, the biodegradable polymer preferably has an inherent viscosity of less than 0.4 dL/g, more preferably 0.35 dL/g or less, more preferably 0.30 dL/g or less, and more preferably 0.25 dL/g or less.

In one embodiment, the polymeric component of the single component system comprises an unblocked polymer of poly(lactide-co-glycolide), polylactide or polyglycolide. In another embodiment, the polymeric component of the single component system comprises a poly(lactide-co-glycolide) that is from 60/40 to 50/50 mole % poly(lactide-co-glycolide), preferably 50/50 mole % poly(lactide-co-glycolide). In another embodiment, the poly(lactide-co-glycolide) has an inherent viscosity of from 0.39 to 0.49 dL/g in chloroform or hexafluoroisopropanol, preferably 0.39 dL/g in hexafluoroisopropanol.

In the case of the blend and single component system, in one embodiment, the encapsulated bioactive agent can be mixed with another encapsulated bioactive agent prepared from a different polymeric composition and/or bioactive agent of the invention. In one embodiment, two or more encapsulated bioactive agents of the present invention can be prepared with two or more polymeric compositions with each comprising a polymer with a molecular weight of less than 7000 daltons. Procedures for combining two or more encapsulated bioactive agents are known in the art (e.g. Men et al. (Vaccine, 1995, 13(7), Peyer's patch 683–689)).

General techniques for the preparation of the single and blend component encapsulated structures are known to those of skill in the art. See, e.g., U.S. Pat. No. 5,407,609 to Tice et al., Grandfils et al. (Journal of Controlled Release, 1996, Peyer's patch 109–122), Bodmeier et al.(International Journal of Pharmaceutics, 1989, Vol. 51, 1–8), and European Patent No. A1 0,058, 481 to Hutchinson.

The preparation of the single and blend component systems can involve the addition of a surfactant to the processing media and/or to a solution of the polymeric composition with the bioactive agent. The residue of such a surfactant will typically remain in the polymeric composition upon formation of the encapsulated agent. The surfactant can be cationic, anionic or nonionic. Examples of useful surfactants include but are not limited to carboxymethyl cellulose, gelatin, poly(vinyl pyrrolidone), poly(ethylene glycol), Tween 80, Tween 20, polyvinyl alcohol or mixtures thereof. The surfactant, preferably, should not hinder the biodegradation of the polymeric composition and release of the bioactive agent. The surfactant should not hinder the uptake of water by the polymeric composition. For example, a surfactant that is used frequently in the prior art is polyvinyl alcohol (PVA). PVA can form a coating on the encapsulated bioactive agent, which may prevent or impede the polymeric composition from biodegrading and the release of the bioactive agent. In one embodiment, the surfactant can be incorporated into the encapsulated bioactive agent. When the surfactant is incorporated into the encapsulated bioactive agent, biodegradation of the encapsulated bioactive agent can occur via osmotic rupture. In a preferred embodiment, the surfactants of the present invention are not incorporated into the encapsulated bioactive agent, but are removed from the surface of the polymeric composition by washing the resultant polymeric composition with water.

During the process for encapsulating the bioactive agent, the size of the resultant particle can be regulated. In one embodiment, the encapsulated structure is less than 300 im in average diameter. In another embodiment, the encapsulated structure is from 20 im to 200 im in average diameter; in another embodiment the encapsulated structure is from 20 im to 80 im in average diameter. In another embodiment, the encapsulated structure is from 1 im to 15 im in average diameter. In a preferred embodiment, the encapsulated structure is from 1 im to 10 im in average diameter. In another embodiment, the encapsulated structure is less than 15 im in average diameter, less than 10 im in average diameter, less than 5 im in average diameter or less than 1 im to preferably 0.1 im in average diameter. The encapsulated bioactive agent can be prepared as a microparticle, microcapsule, microsphere, nanoparticle, nanocapsule, nanosphere or any other encapsulated structure.

In a preferred embodiment, when the bioactive agent comprises an antigen or a nucleic acid encoding the antigen, the encapsulated structure is less than 10 im or from 1 im to 10 im in average diameter. Such a microsphere is likely to be taken up quickly by a macrophage. In another preferred embodiment, when the bioactive agent is an adjuvant, the encapsulated structure is from 1 im to 300 im in average diameter, such as from 20 im to 200 im in average diameter, and more preferably, from 20 im to 80 im in average diameter.

INDUCING OR POTENTIATING AN IMMUNE RESPONSE USING A BLEND OR SINGLE COMPONENT COMPOSITION

The present invention additionally provides methods of utilizing the compositions of the present invention to induce or potentiate an immune response. In any such method for inducing an immune response, the composition comprises an antigen, or nucleic acid functionally encoding the antigen, as the bioactive agent. In any such method for potentiating an immune response, the bioactive agent can comprise, for example, an antigen, an adjuvant or both. Additionally, when the bioactive agent comprises an antigen, the composition can further comprise a nonencapsulated adjuvant. Additionally, a composition wherein the bioactive agent comprises an adjuvant can be administered to a subject wherein the subject has been independently exposed to an antigen to which an immune response is to be induced or potentiated.

The present invention further provides a method of inducing a CTL response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a CTL response is measurable within fourteen days of a single administration at a level of at least 30% cytotoxicity, thereby inducing the CTL response in the subject.

The present invention also provides a method of inducing a T helper cell response in a subject, comprising administering to the subject an effective amount of a composition comprising administering an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that a T helper cell response is measurable within fourteen days of a single administration at a level of at least two-fold over background as measured by T cell proliferation or cytokine induction, thereby inducing the T helper cell response in the subject.

Also provided is a method of inducing a neutralizing antibody response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within fourteen days of a second or subsequent administration, thereby inducing the neutralizing antibody response in the subject.

Additionally provided is a method of inducing a neutralizing antibody response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of antigen or nucleic acid release such that the neutralizing antibody response is detectable within thirty days of a single administration, thereby inducing the neutralizing antibody response in the subject.

Further provided by the present invention is a method of potentiating a preexisting CTL response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated CTL response is measurable within fourteen days of a single administration at a level greater than the preexisting CTL response, thereby potentiating the preexisting CTL response in the subject.

The present invention further provides a method of potentiating a preexisting T helper cell response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated T helper cell response is measurable within fourteen days of a single administration at a level greater than the preexisting T helper cell response, thereby potentiating the preexisting T helper response in the subject.

Further provided by the present invention is a method of potentiating a preexisting neutralizing antibody response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within fourteen days of a second or subsequent administration at a level greater than the preexisting neutralizing antibody response, thereby potentiating the preexisting neutralizing antibody response in the subject.

The present invention also provides a method of potentiating a neutralizing antibody response to an antigen in a subject, comprising administering to the subject an effective amount of a composition comprising a bioactive agent encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

The polymeric composition can further provide kinetics of bioactive agent release such that the potentiated neutralizing antibody response is detectable within thirty days of a single administration at a level greater than the preexisting neutralizing antibody response, thereby potentiating the preexisting neutralizing antibody response in the subject.

The invention further relates to a method of inducing a CTL, T helper or neutralizing antibody response in a subject, comprising administering to the subject an effective amount of a composition comprising an antigen, or nucleic acid functionally encoding the antigen, encapsulated in a polymeric composition, wherein the polymeric composition comprises a biodegradable polymer with a molecular weight of less than or equal to 7000 daltons.

The invention further relates to a method of inducing a CTL, T helper or neutralizing antibody response in a subject, comprising administering to the subject an effective amount of a composition comprising an antigen, or nucleic acid functionally encoding the antigen, encapsulated in a polymeric composition, wherein the polymeric composition comprises a biodegradable polymer with an inherent viscosity of less than 0.4 dL/g.

The invention further relates to a method for inducing a CTL, T helper cell or neutralizing antibody response in a subject, comprising administering to the subject an effective amount of a composition comprising an antigen or nucleic acid encoding the antigen, encapsulated in a polymeric composition, wherein the polymeric composition comprises an unblocked polymer of poly(lactide-co-glycolide), polylactide or polyglycolide.

The invention further relates to a method of potentiating a CTL, T helper or neutralizing antibody response in a subject, comprising administering to the subject an effective amount of a composition comprising a bioactive agent encapsulated in a polymeric composition, wherein the polymeric composition comprises a biodegradable polymer with a molecular weight of less than or equal to 7000 daltons.

The invention further relates to a method of potentiating a CTL, T helper or neutralizing antibody response in a subject, comprising administering to the subject an effective amount of a composition comprising a bioactive agent encapsulated in a polymeric composition, wherein the polymeric composition comprises a biodegradable polymer with an inherent viscosity of less than 0.4 dL/g.

The invention further relates to a method for potentiating a CTL, T helper cell or neutralizing antibody response in a subject, comprising a bioactive agent capable of potentiating a CTL, T helper cell or neutralizing antibody response encapsulated in a polymeric composition, wherein the polymeric composition comprises an unblocked polymer of poly(lactide-co-glycolide), polylactide or polyglycolide.

The invention further relates to a composition for inducing a CTL, T helper or neutralizing antibody response in a subject, comprising an effective amount of a composition comprising an antigen, or nucleic acid functionally encoding the antigen, encapsulated in a polymeric composition, wherein the polymeric composition comprises a biodegradable polymer with a molecular weight of less than or equal to 7000 daltons.

The invention further relates to a composition for inducing a CTL, T helper or neutralizing antibody response in a subject, comprising an effective amount of a composition comprising an antigen, or nucleic acid functionally encoding the antigen, encapsulated in a polymeric composition, wherein the polymeric composition comprises a biodegradable polymer with an inherent viscosity of less than 0.4 dL/g.

The invention further relates to a composition for inducing a CTL, T helper cell or neutralizing antibody response in a subject, comprising an effective amount of a composition comprising an antigen or nucleic acid encoding the antigen, encapsulated in a polymeric composition, wherein the polymeric composition comprises an unblocked polymer of poly(lactide-co-glycolide), polylactide or polyglycolide.

Preferably, the single component systems discussed above achieve the same or similar level of immune (CTL, T helper cell and neutralizing antibody) response as the blend systems described above.

As discussed above, such inducement or potentiation can readily be determined by any of several standard methods. An immune response can include one or more of the following: B-cell responses, including production of antibodies specific for the bioactive agent and cytokine release, and cytotoxic T-cell responses. The introduction of antigens into the phagocytic pathways is attractive for vaccine applications. Antigens entering these pathways can presumably be presented on both MHC class I and class II molecules and elicit concomitant $CD8^+$ and $CD4^+$ T cell immunity. Therefore, the two major arms of the T cell immune response are stimulated. Moreover, under these conditions the $CD4^+$ T cell response has been shown to help the generation of CTL by allowing the CTL and T helper cell to cluster and interact around antigen-presenting cells (APCs), a critical step for $CD4^+$ T cell help. The present method advantageously provides methods that promote rapid release of the bioactive agent from the composition, thus providing a method of introducing the bioactive agent into the phagocytic/cytosolic pathways and eliciting MHC class I-mediated responses in addition to MHC class II-mediated immune responses.

The polymeric composition of the present invention used to encapsulate the bioactive agent is biocompatible. In one embodiment, the degradation products of the polymeric composition are lactic acid and glycolic acid, which are natural metabolites. Encapsulation of antigens using the polymeric compositions of the present invention permits antigens to be delivered in a non-chemically modified form within polymeric vehicles and carriers.

The encapsulated bioactive agent is typically rapidly released once phagocytized and thus released inside the cell. To achieve rapid release in a cell, a preferred composition is one having a microsphere structure of less than 10 im or alternately from 1 to 10 im average diameter. By increasing the size of the encapsulated bioactive agent (greater than 10 im), uptake of the encapsulated agent by the cell decreases, which results in the release of the bioactive agent outside the cell. In a preferred embodiment, the bioactive agent is substantially found inside the encapsulated structure prior to phagocytosis. By "substantially" found inside the structure is meant that at least about 0.1%–50%, preferably at least 20%, more preferably at least 40%, more preferably at least 50%, and even more preferably at least 70% of the originally delivered agent in the composition is still found inside the structure. As discussed above, uptake of a composition of either the blend or single component system can be regulated by size of the microsphere structure, i.e., diameter of the microsphere. The kinetics of release of the bioactive agent from the formulation can be manipulated by several parameters. In the case of the blend component system, the kinetics of release, i.e. the rapid release, of the bioactive agent inside the cell can be regulated by, in addition to microsphere structure diameter, 1) varying the amount component (a) relative to component (b); 2) varying the composition of component (b) as well as the molecular weight of (b); 3) increasing or decreasing the solubility of component (b); 4) loading and type of antigen; 5) the type of surfactant used; 6) whether the component (a) and/or (b) is blocked or unblocked; 7) the presence of other additives; 8) the porosity of the encapsulated bioactive agent; and 9) when glycolide and lactide are selected, the mole %ratio of glycolide and lactide used to prepare components (a) and/or (b). Component (a) can also contribute to the release of the bioactive agent from the polymeric composition; however, component (b) typically ultimately determines the kinetics of release of the bioactive agent.

If rapidly released outside the cell, the bioactive agent is preferably rapidly released close to the cell for rapid uptake of the bioactive agent. A preferred composition for rapid release outside the cell is one having a microsphere structure of greater than 10 im average diameter, such as between 20 and 300 im average diameter, between 20 and 200 im average diameter, or between 20 and 80 im average diameter. Of course, in any composition, some agent is typically released prior to uptake by the cell.

The blend and single component systems of the present invention are capable of inducing or potentiating an immune response. "Immune response" is defined herein to encompass a T- and B-cell response as described above. Moreover, the term "immune response" is not intended to involve or encompass drug delivery (i.e. delivery of non-immunological response inducing or potentiating substances). By "drug" or "pharmaceutical" is meant a substance that does not induce or potentiate an immune response, as known in the art.

In another embodiment, the blend and single component systems are capable of inducing or potentiating a T-cell response, preferably a cytotoxic T-cell response. The blend and single component systems thus can be utilized to induce or potentiate activation of CD8-positive lymphocytes. One advantage of the present invention is that the use of an encapsulated bioactive agent enhances a T-cell response when compared to a bioactive agent that is not encapsulated or that is not as rapidly releasing as the invention.

In yet another embodiment, the blend and single component system can induce or potentiate a neutralizing antibody response.

In one embodiment, once inside the cell, the encapsulated agent is rapidly released. As described earlier, the kinetics of release is dependent upon the components used to prepare the polymeric composition. Because the encapsulated bioactive agent rapidly releases the bioactive agent substantially inside the cell preferentially as compared to outside the cell, it is possible to use a lower dosage of the bioactive agent in order to achieve an immune response.

Once the encapsulated bioactive agent has been incorporated into the cell, the CTL response can be tailored by the selection of the polymeric composition. In one embodiment, an early CTL response can be generated. An early CTL response is defined as a CTL response that can be measured less than or equal to fourteen days upon administration of the encapsulated bioactive agent. In a preferred embodiment, the encapsulated bioactive agent elicits an early CTL response within seven days. In another embodiment, the encapsulated bioactive agent can produce a late CTL response. A late CTL response is defined as a measurable CTL response after fourteen days of administration but not greater than 30 days, preferably 21 days. The measurable CTL response can preferably be at least 30%, 35%, 40%, 45% or 50% cytotoxicity. In a preferred embodiment of the early CTL response, a measurable CTL response of at least 50% can be detected within seven days of administration of the encapsulated bioactive agent. In another preferred embodiment, an early CTL response of at least 50% can be produced from a single administration of the encapsulated bioactive agent.

In any method of this invention, one can administer, for example, a composition comprising an antigen or nucleic acid functionally encoding the antigen, encapsulated in the polymeric composition; a composition comprising an antigen or nucleic acid functionally encoding the antigen, and an adjuvant encapsulated in the polymeric composition; a composition comprising an adjuvant encapsulated in the polymeric composition. In another embodiment, an adjuvant is administered in a composition of the present invention to induce, enhance, or potentiate an immune response to an antigen to which the subject is exposed independently, such as by an administration of the antigen by a prior method, before, simultaneously with or after administration of the composition comprising the adjuvant.

The blend and single component systems can be administered to a subject using a variety of methods known in the art. In one embodiment, the blend and single component systems can be delivered parenterally, by injection, such as intramuscular, intraperitoneal, intravenous or subcutaneous injection, or by inhalation. In another embodiment, the blend and single component systems can be delivered rectally, vaginally, nasally, orally, opthamalically, topically, transdermally or intradermally. When the mode of administration is by injection, the encapsulated bioactive agent may stay at the injection site for up to two weeks, thus providing a depot of antigen that will give sustained release or pulsatile release in vivo. Such a delivery system may allow single-shot vaccine formulations to be produced for antigens which would otherwise require multiple injections to elicit an immune response.

The composition can additionally comprise a pharmaceutically acceptable vehicle. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Examples of such pharmaceutically acceptable vehicle include physiological saline or other suitable vehicles (Arnon, R. (Ed.) Synthetic Vaccines I:83–92, CRC Press, Inc., Boca Raton, Fla., 1987).

The exact amount of such compositions required will vary from subject to subject, depending on the species, age, weight and general condition of the subject, the severity of the disease, infection or condition that is being treated or prevented, the particular compound used, its mode of administration, and the like. Thus, it is not possible to specify an exact amount. However, an appropriate amount may be determined by one of ordinary skill in the art using only routine experimentation given the teachings herein. In one embodiment, the amount of antigen that is administered in an encapsulated form is from 1 ng to 5 mg. In another embodiment, the amount of antigen that is administered in an encapsulated form is from 1 mg to 100 mg. In another embodiment, the amount of antigen that is administered in an encapsulated form is at least about 10 mg. In another embodiment, the amount of adjuvant that is administered in an encapsulated form is from 1 ng to 10 mg. A single administration may be sufficient, depending upon the disease, condition, or infection being treated or prevented; however, it is also contemplated that multiple administrations may be administered. Administrations after the initial administration may be of lower dosage than the initial dosage.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected composition, possibly in combination with a pharmaceutically acceptable carrier and, in addition, may include other medicinal agents, pharmaceutical agents, carriers, adjuvants, diluents, vehicles, etc.

Conventional nontoxic solid vehicles include, for example, pharmaceutical grades of mannitol, lactose, starch, magnesium stearate, sodium saccharin, talc, cellulose, glucose, sucrose, magnesium carbonate, and the like. Encapsulated pharmaceutically administrable compositions in a liquid vehicle can, for example, be prepared by dispersing the encapsulated bioactive agent in a vehicle, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art, for example, see Remington's Pharmaceutical Sciences, E. W. Martin, (ed.), Mack Publishing Co., Easton, Pa., U.S.A.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions.

The blend and single component systems of the present invention can induce or potentiate an immune response in a subject. In one embodiment, the subject is a mammal, reptile, bird or fish. In another embodiment, the subject can be a human or another animal, wherein the animal can particularly be a domestic, food producing or wild animal. Examples of domestic animals include but are not limited to dogs, cats, horses or birds. Examples of food producing animals include but are not limited to cows, pigs, chickens or sheep. Examples of wild animals include but are not limited to zoological animals such as lions, tigers, elephants, monkeys or bears.

The present invention is more particularly described in the following examples which are intended as illustrative only since numerous modifications and variations therein will be apparent to those skilled in the art.

I. EXAMPLES

The following examples are put forth so to provide those of ordinary skill in the art with a complete disclosure and description of how the compositions and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at or near room temperature and pressure is at or near atmospheric.

PREPARATION OF ENCAPSULATED BIOACTIVE AGENTS

Bioactive agents used:

Ovalbumin(OVA)

Grade VII Ovalbumin(OVA) was purchased from Sigma Chemical Company, St. Louis, Mo. and used without further purification.

P815-1(TRA-4)

A 28 amino acid peptide containing the P1A epitope, consisting of residues 28–49 of the P815 antigen with three lysine residues were added to both the C- and N- termini of the sequence to enhance solubility. P1A is a well defined tumor antigen which is expressed on DBA/2 derived P815 tumor cells and also by several DBA/2 normal tissues. A nine amino acid peptide consisting of residues 35–43 of the P815 antigen was also produced. These peptides were synthesized on a Millipore 9050 Plus peptide synthesizer using HBTU (O-Benzotriazole-N,N,N¢,N¢-tetramethyuronium hexafluorophosphate) activation. Cleavage of the peptides from the solid support was carried out using the following mixture: trifluoroacetic acid:ethanedithiol:thioanisole::water:phenol (40:1:2:2:3). After cleaving for two hours, the peptides were precipitated in cold ether. The crude peptides were then purified by C18 reverse phase HPLC and characterized by mass spectrometry prior to use.

Example 1

Bioactive Agent: Ovalbumin

Polymer: 50:50 DL-PLG (503H)

Surfactant: Carboxymethyl cellulose (CMC)

A polymer solution was prepared by dissolving 2.0 g of 50:50 DL-PLG (503H, Boehringer Ingelheim) (PLG is poly(lactide-co-glycolide) with an inherent viscosity of 0.39 dL/g in hexafluoroisopropanol in 7.5 g of ethyl acetate. Next, approximately 25 mg of Ovalbumin was dissolved in 0.5 mL of sterile water. The Ovalbumin solution was added to the polymer solution while it was being homogenized with a Brinkmann Polytron (Model 10, PTA-10S probe, Brinkmann Instrument Co., Westbury, N.Y.).

In a separate container, 280 g of 1.4 wt % aqueous carboxymethyl cellulose, which was saturated with ethyl acetate, was equilibrated to 20±2° C. The standard mixing head of a Silverson Laboratory Mixer (Silverson Machines Inc., East Longmeadow, Mass.) was positioned beneath the surface of the CMC solution.

With the Silverson mixer operating at a stir rate of 3600±50 rpm, the Ovalbumin/polymer emulsion was immediately transferred to the CMC solution. The resulting water-in-oil-in-water emulsion was stirred for 45 seconds, after which the emulsion was transferred to a 5.2 L of sterile water and stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 40 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 40 minutes. This washing process was repeated one additional time, after which the microspheres were suspended in a total volume of approximately 800 mL of sterile water. a total of 500 mg of mannitol was added to the suspension, which was then divided equally into two 1-L freeze-drying flasks. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

Example 2

Bioactive Agent: Ovalbumin

Polymer: 50:50 DL-PLG (503H)

Surfactant: Carboxymethyl cellulose (CMC) and Tween 80

A polymer solution was prepared by dissolving 1.5 g of 50:50 DL-PLG (503H, Boehringer Ingelheim) with an inherent viscosity of 0.39 dL/g in hexafluoroisopropanol in 5.7 g of ethyl acetate. Next, approximately 12 mg of Ovalbumin was dissolved in 0.5 mL of sterile water. The Ovalbumin solution was added to the polymer solution while the polymer solution was being homogenized with a Brinkmann Polytron (Model 10, PTA-10S probe, Brinkmann Instrument Co., Westbury, N.Y.).

In a separate container, a solution consisting of 280 g of 1.33 wt % aqueous carboxymethyl cellulose containing 0.05 wt % polysorbate (Tween 80) was maintained at 18±2° C. This solution was saturated with ethyl acetate. The standard mixing head of a Silverson Laboratory Mixer (Silverson Machines Inc., East Longmeadow, Mass.) was positioned beneath the surface of the CMC/Tween solution.

With the Silverson mixer operating at a stir rate of 4100±50 rpm, the Ovalbumin/polymer emulsion was immediately transferred to the CMC/Tween solution. The resulting water-in-oil-in-water emulsion was stirred for 45 seconds, after which the emulsion was transferred to a 5.2 L of sterile water being stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 45 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 50 minutes. The supernatant was then removed. The microspheres were resuspended in a minimal volume of sterile water and a total of 350 mg of mannitol were added. The microspheres were then rinsed into a 1-L freeze-drying flask and diluted to a total volume of approximately 400 mL. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

Example 3

Bioactive Agent: Ovalbumin
Polymer Blend: 60:40 DL-PLG/DL-lactide(70/30)
Surfactant: Poly(vinyl alcohol)(PVA)—1.0 wt %
Carboxymethyl cellulose (CMC)—0.7 wt %

A polymer solution was prepared by dissolving 1.05 g of 60:40 DL-PLG (Birmingham Polymers Inc.) with an inherent viscosity of 0.49 dL/g in chloroform and 0.45 g of DL-lactide (R104, Boehringer Ingelheim) with a molecular weight of 2000 in 5.5 g of ethyl acetate. Next, approximately 12.5 mg of Ovalbumin was dissolved in 0.5 mL of sterile water. The Ovalbumin solution was added to the polymer solution while it was being homogenized with a Brinkmann Polytron (Model 10, PTA-10S probe, Brinkmann Instrument Co., Westbury, N.Y.).

In a separate container, 280 g of an aqueous solution consisting of 1.0 wt % poly(vinyl alcohol)(PVA) and 0.7 wt % carboxymethyl cellulose (CMC), which was saturated with ethyl acetate, was equilibrated to 12±2° C. The standard mixing head of a Silverson Laboratory Mixer (Silverson Machines Inc., East Longmeadow, Mass.) was positioned beneath the surface of the PVA/CMC solution.

With the Silverson mixer operating at a stir rate of 3850±50 rpm, the Ovalbumin/polymer emulsion was immediately transferred to the PVA/CMC solution. The resulting water-in-oil-in-water emulsion was stirred for 45 seconds, after which the emulsion was transferred to a 5.2 L of sterile water being stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 45 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 55 minutes. This washing process was repeated one additional time, after which the microspheres were suspended in a total volume of approximately 400 mL of sterile water. a total of 300 mg of mannitol was added to the suspension, which was then transferred to a 1-L freeze-drying flask. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

Example 4

Bioactive Agent: Ovalbumin
Polymer Blend: 50:50/DL-lactide(80/20)
Surfactant: Poly(vinyl alcohol)(PVA)—1.0 wt %
Carboxymethyl cellulose (CMC)—0.7 wt %

A polymer solution was prepared by dissolving 0.8 g of 50:50 DL-PLG (Birmingham Polymers, Inc.) with an inherent viscosity of 0.39 dL/g in hexafluoroisopropanol and 0.20 g of DL-lactide (R104, Boehringer Ingelheim) with a molecular weight of 2000 in 4.0 g of ethyl acetate. Next, approximately 9.3 mg of Ovalbumin was dissolved in 0.5 mL of sterile water. The Ovalbumin solution was added to the polymer solution while it was being homogenized with a Brinkmann Polytron (Model 10, PTA-10S probe, Brinkmann Instrument Co., Westbury, N.Y.).

In a separate container, 280 g of an aqueous solution consisting of 1.0 wt % poly(vinyl alcohol)(PVA) and 0.7 wt % carboxymethyl cellulose (CMC), which was saturated with ethyl acetate, was equilibrated to 17±2° C. The standard mixing head of a Silverson Laboratory Mixer (Silverson Machines Inc., East Longmeadow, Mass.) was positioned beneath the surface of the PVA/CMC solution.

With the Silverson mixer operating at a stir rate of 3950±50 rpm, the Ovalbumin/polymer emulsion was immediately transferred to the PVA/CMC solution. The resulting water-in-oil-in-water emulsion was stirred for 45 seconds, after which the emulsion was transferred to a 5.2 L of sterile water being stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 50 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 60 minutes. This washing process was repeated one additional time, after which the microspheres were suspended in a total volume of approximately 400 mL of sterile water. a total of 250 mg of mannitol was added to the suspension which was then transferred to a 1-L freeze-drying flask. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

Example 5

Bioactive Agent: P815-1
Polymer: 50:50 DL-PLG (503H)
Surfactant: Carboxymethyl cellulose (CMC)

A polymer solution was prepared by dissolving 1.5 g of 50:50 DL-PLG (503H, Boehringer Ingelheim) with an inherent viscosity of 0.39 dL/g in hexafluoroisopropanol in 5.6 g of ethyl acetate. Next, approximately 15 mg of P815-1 was dissolved in 0.4 mL of sterile water. The P815-1 solution was added to the polymer solution while it was being homogenized with a Brinkmann Polytron (Model 10, PTA-10S probe, Brinkmann Instrument Co., Westbury, N.Y.).

In a separate container, 280 g of 1.4 wt % aqueous carboxymethyl cellulose, which was saturated with ethyl acetate, was equilibrated to 18±2° C. The standard mixing head equipped with a Silverson Laboratory Mixer (Silverson Machines Inc., East Longmeadow, Mass.) was positioned beneath the surface of the CMC solution.

With the Silverson mixer operating at a stir rate of 3850±50 rpm, the P815-1/polymer emulsion was immediately transferred to the CMC solution. The resulting water-in-oil-in-water emulsion was stirred for 45 seconds, after which the emulsion was transferred to a 5.2 L of sterile water being stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 40 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 45 minutes. This washing process was repeated one additional time, after which the microspheres were suspended in a total volume of approximately 800 mL of sterile water. a total of 400 mg of mannitol was added to the suspension, which was then divided equally into two 1-L freeze-drying flasks. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

Example 6

Bioactive Agent: P815-1
Polymer: 50:50 DL-PLG (503H)
Surfactant: Carboxymethyl cellulose (CMC) and Tween A polymer solution was prepared by dissolving 1.5 g of 50:50 DL-PLG (503H, Boehringer Ingelheim) with an inherent viscosity of 0.39 dL/g in hexafluoroisopropanol in 5.7 g ethyl acetate. Next, approximately 14.5 mg of P815-1 was dissolved in 0.5 mL of sterile water. The P815-1 solution was added to the polymer solution while it was being homogenized with a Brinkmann Polytron(Model 10, PTA-10S probe, Brinkmann Instrument Co., Westbury, N.Y.).

In a separate container, a solution consisting of 280 g of 1.0 wt % aqueous carboxymethyl cellulose containing 0.03 wt % polysorbate (Tween 80) was maintained at 18±2° C. This solution was saturated with ethyl acetate. The standard mixing head of a Silverson Laboratory Mixer (Silverson Machines, Inc., East Longmeadow, Mass.) was positioned beneath the surface of the CMC/Tween solution.

With the Silverson mixer operating at a stir rate of 4000±50 rpm, the P815-1/polymer emulsion was immediately transferred to the CMC/Tween solution. The resulting water-in-oil-in-water emulsion was stirred for 45 seconds, after which the emulsion was transferred to 5.2 L of sterile water which was being stirred with a stainless steel impeller. The microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc., Fullerton, Calif.) for 45 minutes. After centrifuging the suspension, the supernatant was removed. The microspheres were resuspended in additional sterile water. The contents of each centrifuge bottle were diluted to a total volume of approximately 800 mL. The centrifuge bottles were again centrifuged at 4200 rpm for approximately 50 minutes. Again, the supernatant was removed. The microspheres were resuspended in a minimal volume of sterile water and a total of 350 mg of mannitol were added. The microspheres were then rinsed into a 1-L freeze-drying flask and diluted to a total volume of approximately 400 mL. The microsphere suspension was then frozen and lyophilized (FTS Systems, Stone Ridge, N.Y.). The resulting microspheres contained approximately 0.8±0.2 wt % P815-1 and had a diameter of about 5.0 im or less.

Example 7

Bioactive Agent: P815-1
Polymer Blend: 60:40 DL-PLG (80%), DL-lactide (20%)
Surfactant: Poly(vinyl alcohol)(PVA)—1.0 wt %, Carboxymethyl cellulose (CMC)—0.7 wt %

A polymer solution was prepared by dissolving 1.2 g of 60:40 DL-PLG (Birmingham Polymers Inc.) with an inherent viscosity of 0.49 dL/g in chloroform and 0.30 g of DL-lactide (R104, Boehringer Ingelheim) with a molecular weight of 2000 in 5.5 g of ethyl acetate. Next, 15.1 mg of P815-1 was dissolved in 0.5 mL of sterile water. The P815-1 solution was added to the polymer solution while it was being homogenized with a Brinkmann Polytron (Model 10, PTA-10S probe, Brinkmann Instrument Co., Westbury, N.Y.).

In a separate container, 280 g of an aqueous solution consisting of 1.0 wt % poly(vinyl alcohol)(PVA) and 0.7 wt % carboxymethyl cellulose (CMC), which had been saturated with ethyl acetate was equilibrated to 15±2° C. The standard mixing head, of a Silverson Laboratory Mixer (Silverson Machines Inc., East Longmeadow, Mass.) was positioned beneath the surface of the PVA/CMC solution.

With the Silverson mixer operating at a stir rate of 3850±50 rpm, the Ovalbumin/polymer emulsion was immediately transferred to the PVA/CMC solution. The resulting water-in-oil-in-water emulsion was stirred for 45 seconds, after which the emulsion was transferred to a 5.2 L of sterile water being stirred with a stainless steel impeller. The resulting microspheres were stirred in the water for approximately 15 minutes.

The sterile water and microspheres were then transferred to 6, 1-L centrifuge bottles. The bottles were centrifuged at 4200 rpm using a Beckman J6M centrifuge (Beckman Instruments, Inc. Fullerton, Calif.) for 50 minutes. After centrifuging the suspension, the supernatant was removed. The microspheres were resuspended in additional sterile water. The contents of each centrifuge bottle were diluted to a total volume of 800 mL. The centrifuge bottles were again centrifuged at 4200 rpm for 55 minutes. This washing process was repeated one additional time, after which the microspheres were suspended in a total volume of approximately 400 mL of sterile water. a total of 400 mg of mannitol was added to the suspension which was then transferred to a 1-L freeze-drying flask. The microsphere suspension was then frozen and lyophilized (FTS Systems, Stone Ridge, N.Y.). The resulting microspheres contained approximately 0.8±0.2 wt % Ovalbumin and have a diameter of about 5.0 im or less.

IMMUNOLOGICAL EXPERIMENTS

Materials and Methods

Mice

Female C57BL/6 ($H-2^b$) and DBA/2 ($H-2^d$) mice of 6 to 8 weeks of age were purchased from Charles River Laboratories (Boston, Mass.). They were maintained at the animal facility of the Fred Hutchinson Cancer Research Center (Seattle, Wash.).

Antigens and Reagents

Ovalbumin (Grade VII) was purchased from Sigma (St. Louis, Mo.) and was used without further purification.

Anti-CD8 (53-6.7) and anti-CD4 (H129.19) monoclonal antibodies were purchased from Pharmingen (San Diego, Calif.). Peptides used in this study were synthesized on a Millipore 9050 Plus peptide synthesizer through HBTU (O-Benzotriazole-N,N,Ni,Ni-tetramethyluronium hexafluorophosphate) activation, and then cleaved from the solid support with a solution of trifluoroacetic acid:ethanedithiol:thioanisole:water:phenol (40:1:2:2:3). After cleavage, crude peptides were purified by C18 reverse phase HPLC and characterized by mass spectrometry prior to use. Ova peptides were made according to the published sequences of potential epitopes restricted by $H-2K^b$ disclosed in Barber et al. (Journal of Experimental Medicine, 1994, 180, pp 1191–1194). Two tumor associated peptides were made based on the P1A core epitope derived from the P815 tumor, a 28 amino acid long peptide, P815-1, consisting of residues 28–49 of the P1A antigen with 3 lysine residues added to both the C- and N-termini of the sequence (KKKRYSLEEILPYLGWLVFAVVTTSKKK) to enhance solubility and a 9 residue peptide, P815-2, consisting of the exact epitope LPYLGWLV. The control peptide JAK-1 (SYFPEITHI) was synthesized according to Harpur et al. (Immunological Letters, 1993, 35, pp 235–237).

Tumors and Transfectant Cell Lines

EL4 thymoma ($H-2^b$), P815 mastocytoma ($H-2^d$) and P1A antigen negative L1210 ($H-2^d$) lymphocytic leukemia lines were purchased from ATCC (Rockville, Md.). The making of Ova expressing EL4 transfectant EG7.Ova was disclosed in Moore et al. (Cell, 1988, 54, pp 777–785). BMA3.1 was a C57BL/6 derived bone marrow macrophage line. All tissue cultures used an RPMI complete medium supplemented with 10% FCS, 2 mM glutamine, 50 U/ml penicillin, streptomycin, gentamycin and $2'10^{-5}$ M â-mercaptoethanol. EG7.Ova cell line was grown in a selective medium containing 0.4 mg/ml G418.

Formulation and Characterization of Encapsulated Bioactive Agents

All encapsulated bioactive agents used in the immunological studies were prepared using the procedures of Examples 1–7. The microspheres averaged from 2–3 im in diameter and had an antigen content of between 0.5% and 1% (w/w). The microsphere product was characterized using standard methods to determine core loading, homogeneity of encapsulated peptide or protein and also the in vitro release characteristics of the microspheres (Eldridge, J. H. et al. (1993) Semin. Hematol. 30, 16–24; Eldridge, J. H. et al. (1991) Infect. Immun. 59, 2978–2986). Typically, microsphere preparations release in vitro 50% of encapsulated antigen over 4–8 weeks, following an initial burst of <10% of antigen in PBS.

Animal Immunization and In Vitro Stimulation of Effector Population

C57BL/6 mice were immunized subcutaneously with 15–30 μg of soluble Ova or Ova encapsulated in microspheres (Ova/PLG). In the P1A system, DBA/2 mice were similarly immunized with P815-1 peptide alone or P815-1/ PLG. PLG is defined herein as PLG1, which represents the polymeric composition of the single component system, or PLG2a-XX, which represents the polymeric composition of the blend component system. Antigens were suspended in 200 iL of PBS and injected on both flanks of the animal. As controls, mice were immunized with Ova admixed with alum as adjuvant. Fourteen to 21 days after the immunization, splenocytes were prepared as single cell suspensions and $\sim 50'10^6$ cells from each mouse were incubated with $2.5'10^6$ irradiated (200,000 rad) EG7.Ova cells. For anti-P1A response, spleen cells were stimulated with irradiated P815 cells or splenocytes pre-incubated with P815-2 peptide. After five days of culture, CTL activities were measured in a $^{51}Cr$ release cytotoxicity assay as described below.

In Vitro Presentation of Encapsulated Antigen

BMA3.1 macrophage cells were pulsed with 6 mg of Ova/PLG, equivalent concentration of soluble Ova or Ova+ placebo PLG microspheres for 4 hours. Excessive microspheres were removed with repeated washing. The pulsed cells were harvested, washed with PBS and promptly subject to a CTL assay using an established Ova specific CTL line.

Cytotoxic T-Cell Assay

To conduct a CTL, assay, target cells were incubated with $^{51}Cr$ at 100 iCi/$10^6$ cells at 37° C. for 60 min. Labeled cells were washed 2 or 3 times and $1'10^4$ per well of labeled targets were distributed into 96 well plates in a final volume of 200 il/well of RP-10 (RPMI medium with 10% FCS). Various effector:target ratios were used as indicated. After 4 hours of incubation at 37° C., supernatant was collected from test wells using Skatron filter strips and counted on a Packard Cobra II ã counter. Specific lysis was calculated as:

$$\% \text{ specific lysis} = \frac{\text{Experimental release} - \text{Spontaneous release}}{\text{Maximum release} - \text{Spontaneous release}} \times 100$$

To determine peptide specificity of the CTLs, target cells were incubated with 50 μg/ml of peptides in RP-10 for 1 hour, washed three times and then subjected to the same assay procedure described above.

T helper Assay and Cytokine Production

To determine the involvement of the PLG beads in the outcome of the subsets of T helper cells (Th1 or Th2), the cytokines IFN-ã and IL-4 were measured in the culture supernatants of antigen stimulated cells. Briefly, spleen cells or lymph node cells ($3.0 \times 10^6$/ml) from mice immunized with antigens were cultured for 3 days with or without various antigens. Supernatants were collected and the cytokines IFN-ã and IL-4 were quantified by ELISA as described using specific anti-IFN-ã or anti-IL-4 monoclonal antibodies (Pharmingen, San Diego, Calif.). Briefly, IFN-ã is measured using an enzyme-linked immunosorbent assay (ELISA). ELISA plates are coated with an antibody directed to mouse IFN-ã in PBS for six hours at room temperature. Wells were then blocked with PBS containing 1% (W/V) BSA plus 0.1% Tween-20 for 3 hour at room temperature. The plates were washed six times in PBS/0.1% Tween-20, and the samples were diluted 1:2 in PBS/1% BSA/0.1% Tween-20 in the ELISA plates. The plates were incubated overnight at 4° C. The plates were again washed and biotinylated with monoclonal anti-FN-ã or IL-4 diluted in PBS/1% BSA/0.1% Tween-20. The plates were then incubated for two hours at room temperature, washed, and 100 ul (per well) of Streptavidin-HRP (diluted 1:2000 in PBS/1% BSA/0.1%) was added. Tween-20 was then added. After a further 30 minutes of incubation at room temperature, the plates were washed and TMB substrate added. The reaction was stopped after 10 minutes with 1N sulfuric acid. Optical density was determined at 450 nm using 570 nm as a reference wavelength. Fractions that result in both replicates giving an OD two fold greater than the mean OD from cells cultured in medium alone, plus 3 standard deviations, were considered positive.

Similarly, IL-4 was measured by using a pair of monoclonal anti-mouse IL-4 antibodies. Otherwise assays were performed as described above.

T-Cell Depletion Assay

For in vitro depletion experiments, in vivo primed splenocyte cultures were incubated with anti-CD4 or anti-CD8 mAbs immobilized on AIS MicroCELLector T25 culture flask according to the protocol supplied by the manufacturer (Applied Immune Sciences, Inc., Menlo Park, Calif.).

Induction of Specific Antibody Response in Mice

Mice (2–3 per group) were immunized with 5–40 ig of the test antigen with or without encapsulated in PLG beads. As a control, mice were also immunized with the recombinant antigen in alum, CFA or in PBS. Mice were bled 1 week after each immunization. Antibodies recognizing antigens were detected as follows: Plates were coated with 100–500 ng of the test antigen in PBS per well of 96 well PVC plates. They were blocked and 100 il of serial dilutions of sera were added per well and incubated for two hours at room temperature. Plates were washed and HRP conjugated goat anti-mouse IgG was added and incubated for one hour at room temperature. Thereafter, plates were washed and developed with HRP substrate TMB. Optical densities of the color developed were read at 405 nm. Results are expressed as OD405 vs. 1/sera dilution.

Anti-Tumor Immunity Studies

Mice were subcutaneously immunized with 30 ig/mouse of P815-1/PLG, peptide alone or peptide mixed with alum adjuvant. Three weeks after the immunization, they were challenged intradermally on the flank with $5'10^4$ live P815 cells. Tumor occurrence was examined every 3 or 4 days.

SINGLE COMPONENT ENCAPSULATED ANTIGENS

Example 8

The single component encapsulated antigen that was investigated was prepared using the procedure outlined in Example 1, with the polymeric composition denoted as PLG1.

To determine whether antigens encapsulated using a single component system could be introduced into the antigen presentation pathway of the MHC class I molecule, an in vitro system was used in which Ova/PLG1 microspheres were incubated with a macrophage cell line, BMA3.1 ($H-2K^b$) for various lengths of time. The cells were then examined for evidence of particle uptake. The MHC presentation of Ova epitopes was determined by the ability of the Ova specific CTL to recognize BMA3.1 cells preincubated with Ova/PLG1.

As shown in FIG. 1, Ova/PLG1 efficiently sensitized target cells for Ova recognition, BMA3.1 cells incubated with Ova/PLG1 microspheres for 4 hours were efficiently killed by specific CTLs. $1'10^6$ BMA3.1 cells were incubated with an optimal dose of 6 mg of Ova/PLG (-1-) containing about 30 μg of Ova for 4 hr at 37° C. and subjected to CTL recognition by an established Ova specific CTL line. As controls, BMA3.1 cells were also treated with medium alone (-à-), Ova 257–264 peptide (-t-), 30 μg/ml soluble Ova (-o-), 6 mg of placebo PLG1 (-Ä-) or 30 μg/ml Ova mixed with 6 mg PLG1 (-m-) for the same period of time. Specific CTL recognition was observed only when BMA3.1 cells were pre-incubated with Ova/PLG1 and the $H-2K^b$ presented Ova 257–264 peptide.

In this experiment, no CTL recognition of macrophages pulsed with equivalent concentrations of soluble Ova was observed (FIG. 1), indicating that the uptake of soluble protein from the medium by these cells was extremely inefficient. To rule out the possibility that the presence of microparticles in the culture, rather than their encapsulated antigen, might have stimulated antigen uptake by BMA3.1 cells, these cells were also incubated with soluble Ova plus placebo PLG1 microspheres. No CTL recognition above background was observed (FIG. 1). These data suggest that the sensitization of macrophages required particulate antigens.

Example 9

The single component encapsulated antigen that was investigated was prepared using the procedure outlined in Example 1, which is expressed as PLG1, was tested for CTL activity.

To address whether the same Ova/PLG1 could prime specific CTL in vivo, C57BL/6 mice ($H-2^b$) were immunized with either soluble Ova or Ova/PLG. Control mice were also immunized with soluble Ova admixed with placebo PLG1 microspheres (Ova+PLG1) and Ova with alum. To assay CTL activity, splenocytes were harvested two weeks after immunization and stimulated with irradiated EG7.Ova cells.

Figure 2A:
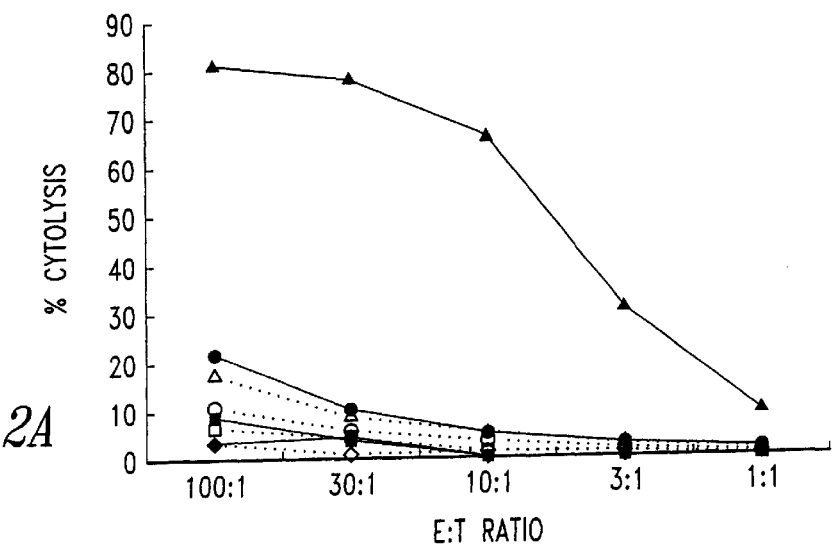

The results in FIG. 2a show that only Ova/PLG1 microsphere immunized mice mounted a strong CTL response. C57BL/6 mice were immunized with Ova/PLG (-Ù-) containing 30 μg of Ova once for two weeks. The resulting effector cells were tested against either EL4 cells (open symbols) or EG7.Ova (closed symbols). No cytotoxicity was observed with effector cells from mice immunized with the same amount of soluble Ova (-t-), Ova plus Alum (-l-) or Ova admixed with PLG microspheres (-n-). The results shown here are typical of over 70 experiments that have been performed so far. In keeping with the in vitro data, no specific CTL elicitation could be detected in mice immunized with any other antigen combination, including Ova admixed with placebo PLG1 microspheres or alum.

Figure 2B:
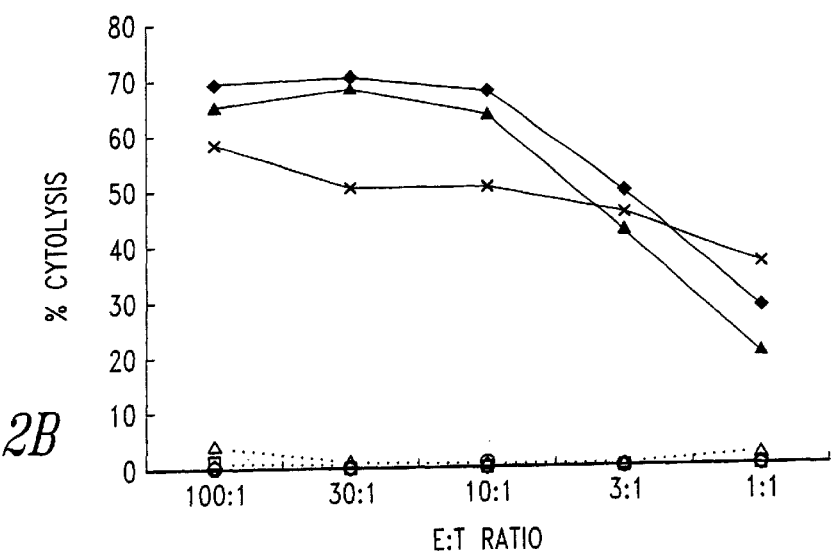

The peptide specificities of the CTL population induced by Ova/PLG1 were further investigated. The same primed CTL population was tested against EL4 cells coated with 6 ovalbumin derived peptides, including the two known immunodominant peptides Ova 257–264 and Ova 55–62 and four others with sequences that conform to the $K^b$ binding motif. The results in FIG. 2b show that Ova/PLG1 primed effector cells contained specificities for both known epitopes, but not against any of the other four putative epitopes. Ova/PLG1 primed effectors recognized EG7.Ova (-t-) and EL4 pulsed with the immune dominant Ova 257–264 (SIINFEKL, -Ù-) and sub-dominant Ova 55–62 (KVVRFDKL, -<<-) epitopes, but not EL4 (-à-) or EL4 pulsed with other four peptides, Ova 12–19 (CFDVFKEL, -Ä-), Ova 25–32 (ENIFYCPI, -l-), Ova 107–114 (AEERYPIL, -m-) and Ova 176–183 (NAIVFKGL, -o-); which conforms to the $H-2K^b$ binding motif.

Figure 2C:
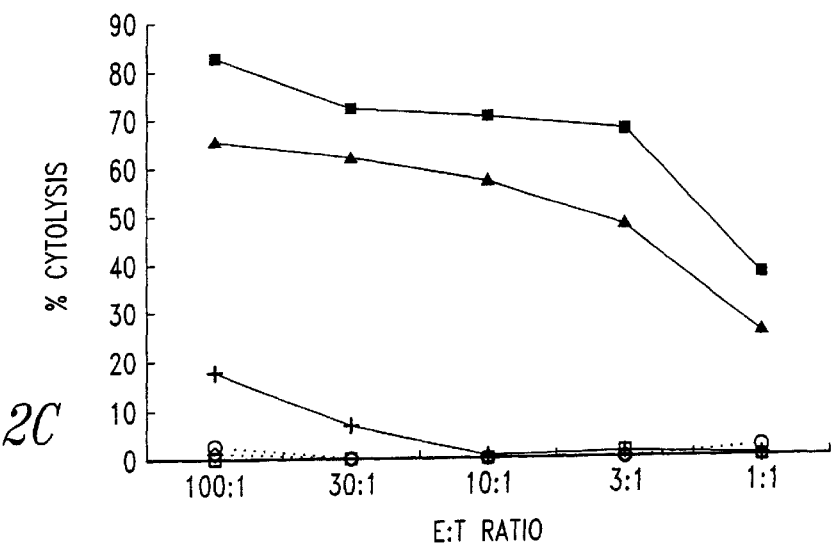
Figure 3A:
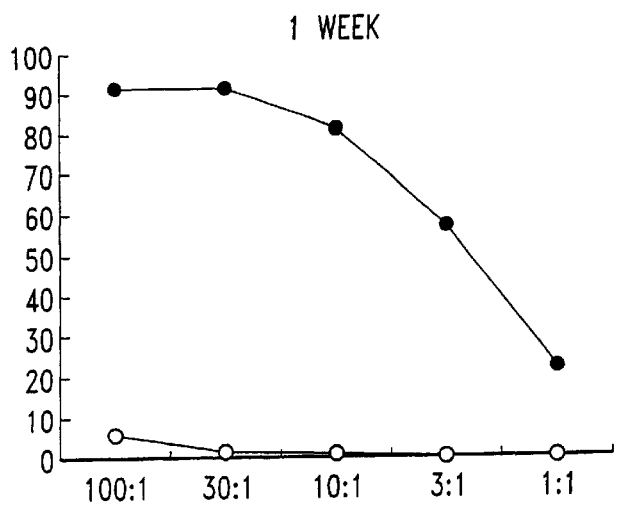
Figure 3B:
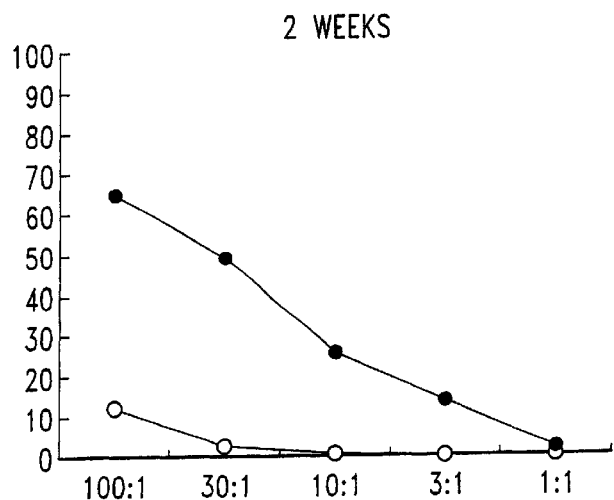
Figure 3C:
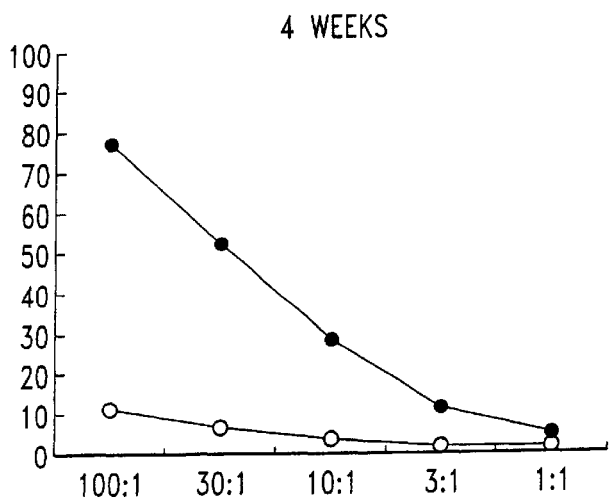
Figure 3D:
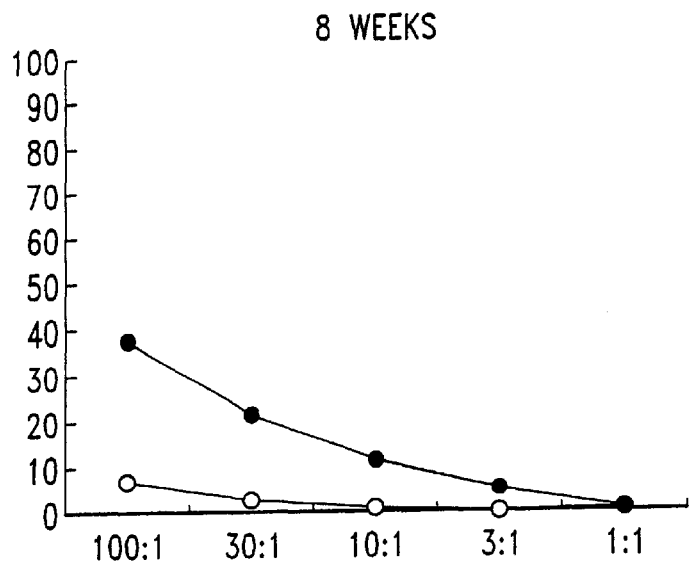
Figure 3E:
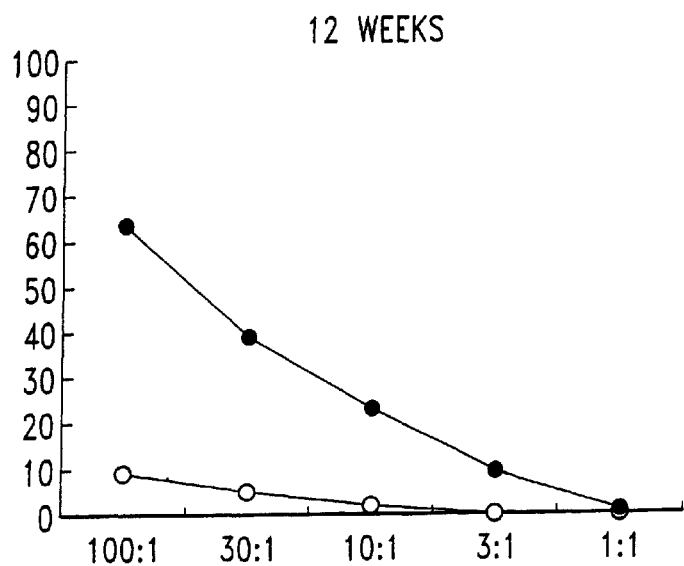

The phenotypes of the Ova/PLG1 induced T cell population were also examined. Ova/PLG1 immunized spleen cells were cultured with irradiated EG7.Ova, and then harvested and depleted of $CD4^+$ or $CD8^+$ T cells by incubation with monoclonal anti-CD4 or anti-CD8 antibodies as described in Materials and Methods. When tested for CTL activity against EG7.Ova cells, depletion of the $CD8^+$, but not $CD4^+$ subpopulation abrogated the CTL response, indicating that the Ova reactive cytolytic activity was $CD8^+$ dependent (FIG. 2c). In vivo primed spleen cells were tested against EL4 (open symbols) or EG7.Ova (closed symbols) without depletion (-n-) or with depletion of $CD4^+$ (-l-) or $CD8^+$ (-t-) T cells are shown in FIG. 2c. Only the depletion of $CD8^+$ population abrogated the cytolytic activity.

To ensure that the Ova/PLG1 elicited CTL response lasted for prolonged period of time, the overall Ova specific CTL activity was monitored in the primed splenocyte population for up to 12 weeks after a single immunization. As shown in FIG. 3, the anti-Ova activity maintained at a high level even 12 weeks after the initial immunization. C57BL/6 mice were immunized once at 30 μg of protein per animal. Mice were sacrificed at different time points as indicated in the figure for CTL activity. Even after 12 weeks, the in vivo primed splenocytes were still able to recognize EG7 (-l-) but not EL4 (-m-) at a high level.

Example 10

The single component encapsulated antigen examined in Example 10 was prepared using the procedure outlined in Example 5, and will be expressed as PLG1.

To further investigate the application of encapsulated bioactive agents to other types of antigen, the above experiment was extended to a tumor associated antigen P1A. The P1A antigen differs significantly from ovalbumin in that it is a self-antigen expressed by both the tumor and some normal tissues. As the full length P1A protein antigen was not readily available, a 28 amino acid peptide containing the CTL epitope was synthesized (P815-1) and encapsulated in PLG1 microspheres. Mice were immunized with these P815-1/PLG microspheres and various controls.

Figure 4A:
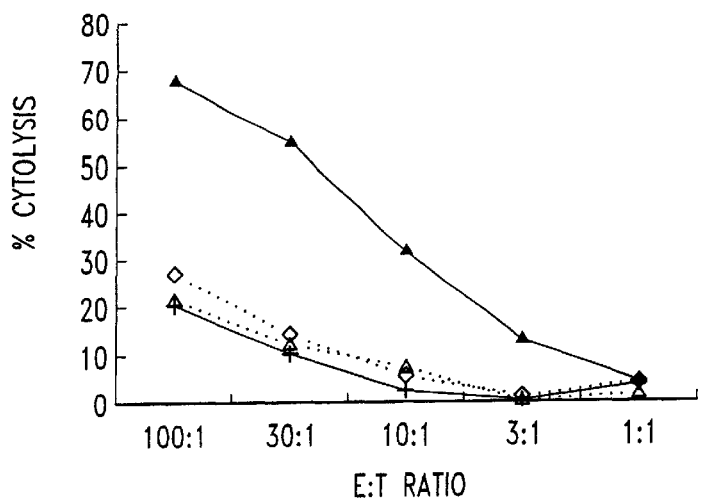

Two weeks of immunization with P815-1/PLG1 resulted in a splenocyte population that was strongly reactive against P815 cells but not syngeneic L1210 cells (FIG. 4a). DBA/2 mice were immunized with 30 µg of soluble P815-1 peptide (-t- and -à-) or the equivalent amount of P815-1/PLG (-Ù- and --). Two weeks after a single immunization, spleen cells were stimulated in vitro for five days with irradiated splenocytes preincubated with P815-2 (LPYLGWLV) peptide. The resulting effector cells showed a specific activity against P815 (closed symbols) but not syngeneic L1210 (open symbols) cells. Minimal CTL priming was seen with soluble P815-1 peptide.

Figure 4B:
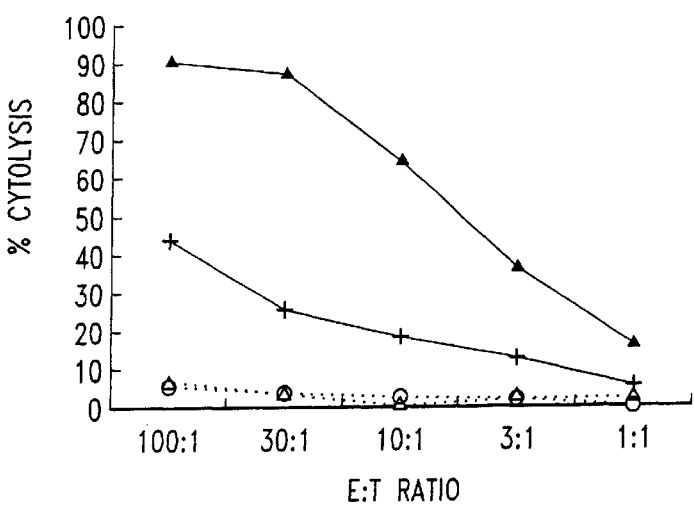

The peptide specificity of the P815-1/PLG1 induced CTL was confirmed to be against the P1A antigen. As shown in FIG. 4b, effector cells only recognized P815 cells expressing P1A antigen (-Ù-). The same effector cells also recognized L1210 cells exposed to the core P1A epitope (-t-) whereas the $H\text{-}2K^d$ restricted control peptide, JAK-1, which was highly expressed on P815 cells, was not recognized. L1210 (-À-) cells alone were not recognized, nor were $H\text{-}2K^d$ restricted JAK-1 kinase peptide (SYFPEITHI, -m-) pulsed L1210 cells.

Figure 4C:
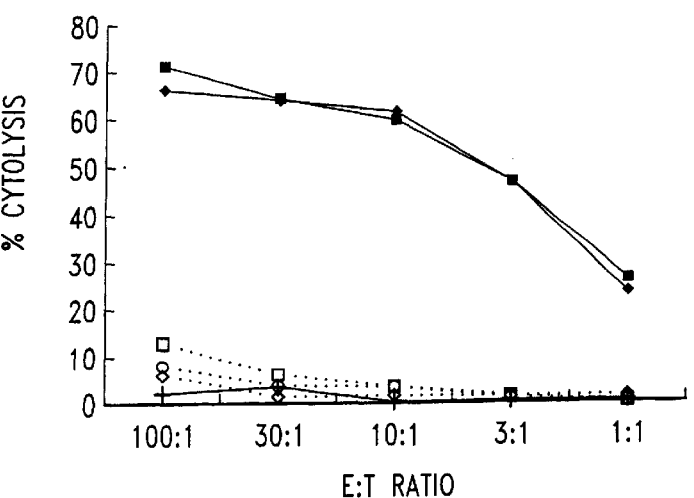

The cytolytic activity was strictly $CD8^+$ dependent as shown by the depletion assay in FIG. 4c. Unseparated (-n- and -o-), $CD4^+$ depleted (-l- and -j-) and $CD8^+$ depleted (-t- and -à-) CTLs were tested against L1210 cells (open symbols) and P815 cells (closed symbols). The data show that P815-1/PLG1 primed effector cells are $CD8^+$ dependent.

Example 11

Figure 5:
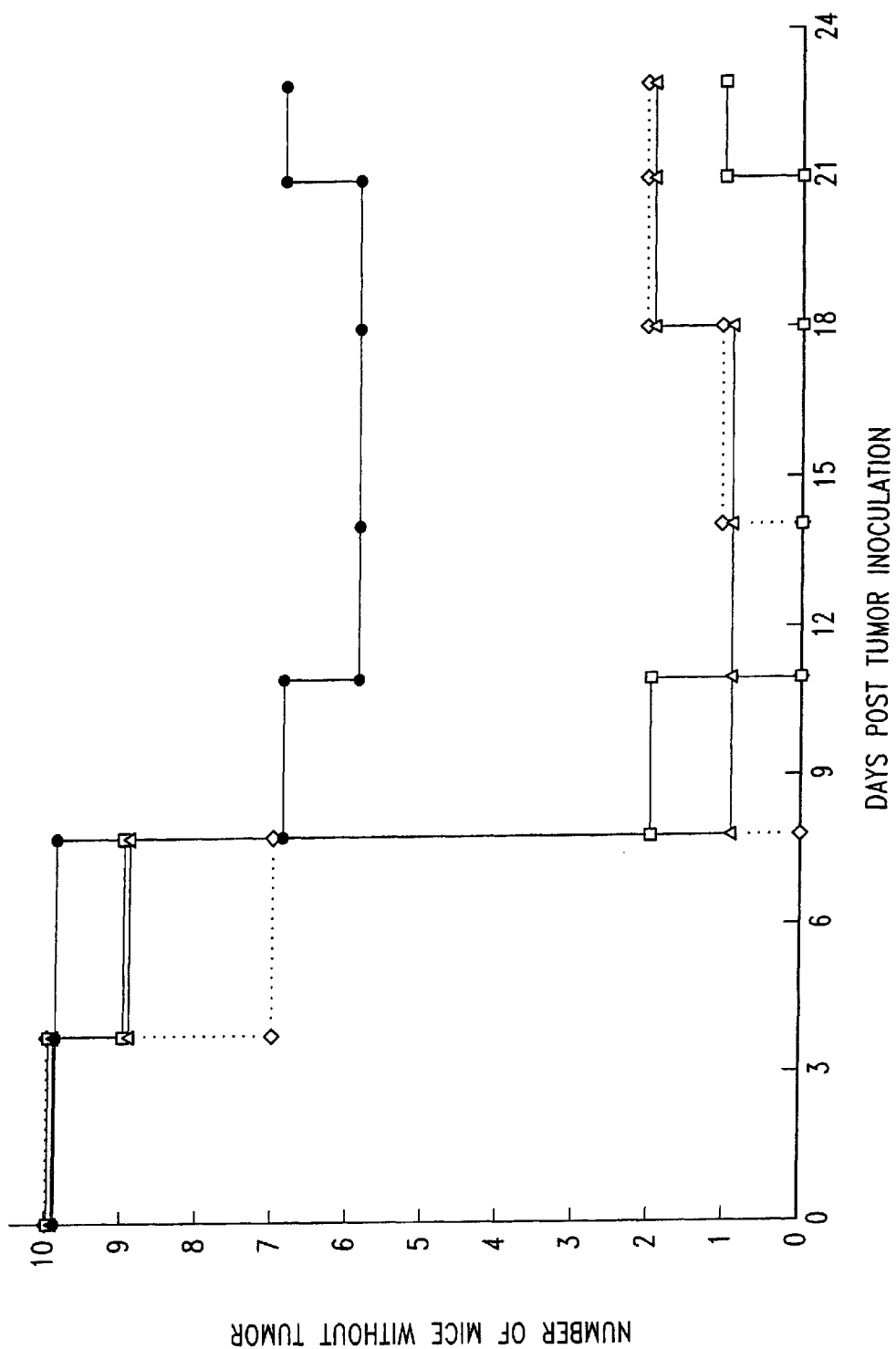
Figure 6A:
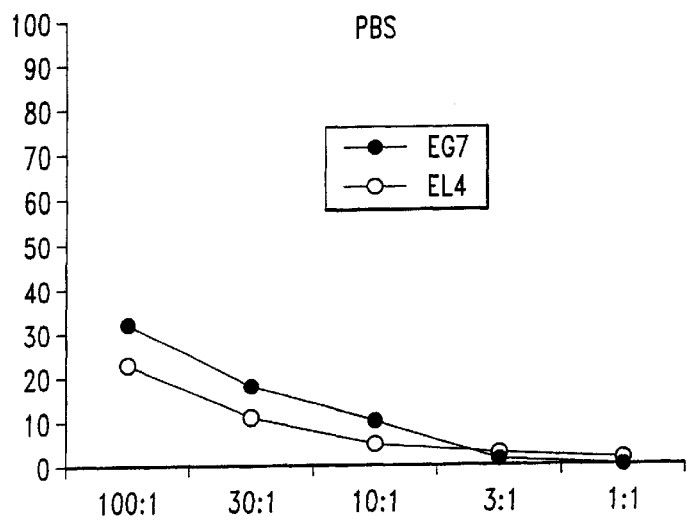
Figure 6B:
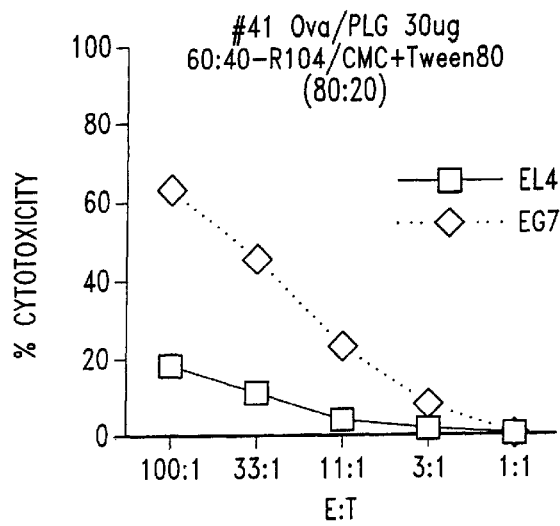
Figure 6C:
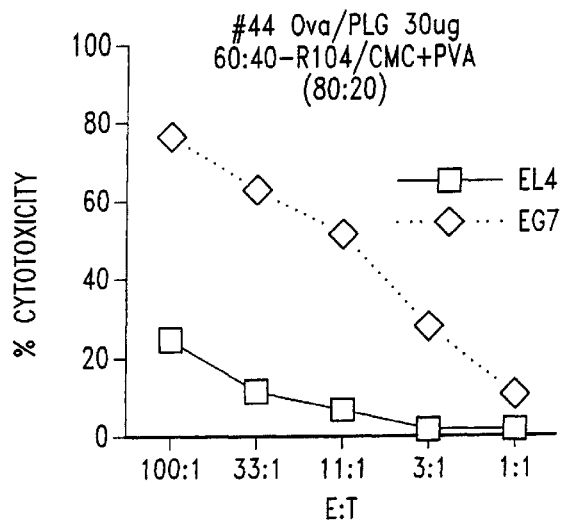
Figure 6D:
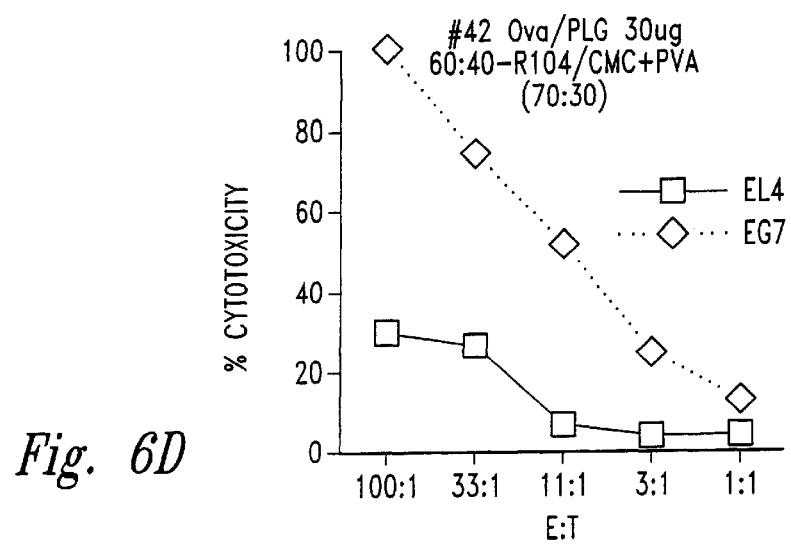
Figure 6E:
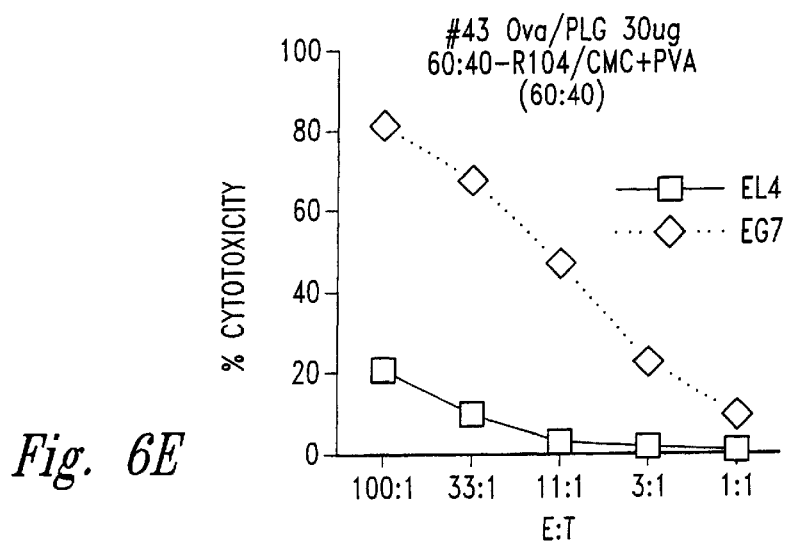
Figure 6F:
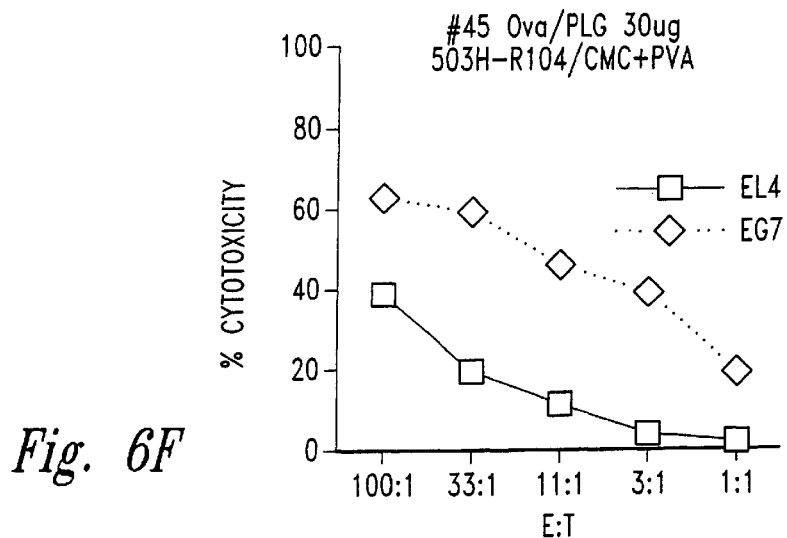
Figure 6G:
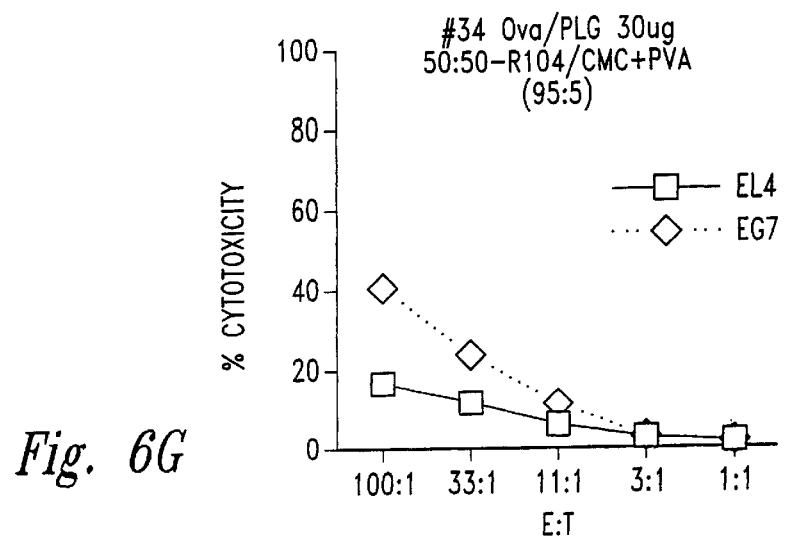
Figure 6H:
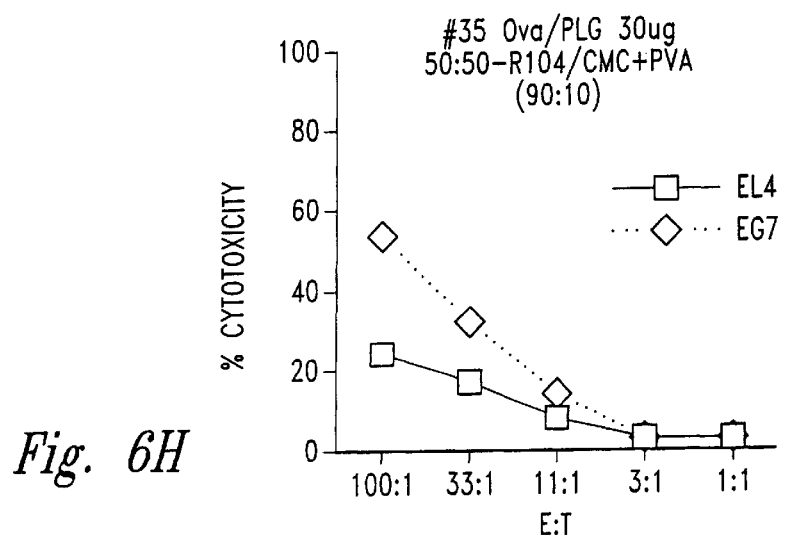
Figure 6I:
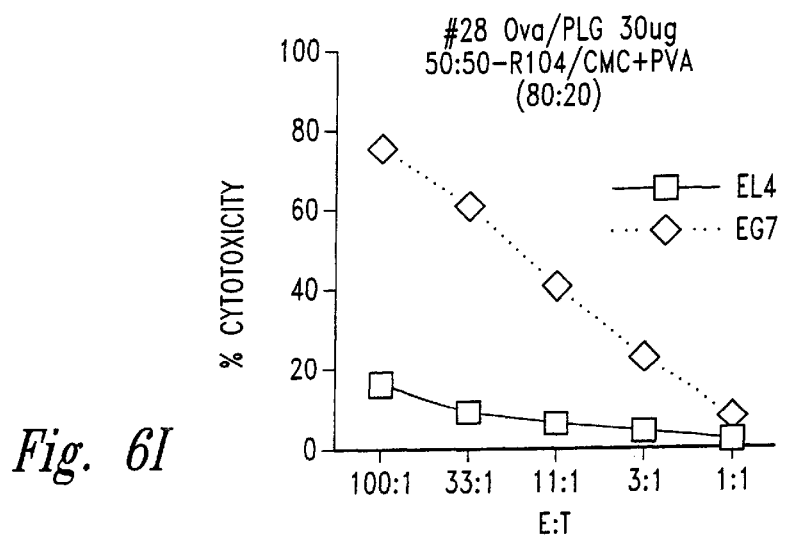

The ability of P815-1/PLG1 microspheres to elicit protective immunity against intradermally inoculated tumor was investigated. Groups of 10 mice were immunized with P815-1/PLG1 and various controls as described above. DBA/2 mice were immunized with PBS (-à-), 30 ig of soluble P815-1 peptide (-o-), P815-1/PLG1 (-l-) microspheres or P815-1 in alum (-À-). Three weeks after the immunization, they were challenged with $5'10^4$ live P815 cells on the flank. 7 out of 10 mice that were immunized with P815-1/PLG1 were protected from tumor occurrence and have remained tumor free for over 90 days. Four weeks after the immunization, mice were challenged with $5'10^4$ per mouse of P815 cells. Once inoculated with tumor cells, mice were closely monitored for tumor progression. After 21 days of observation, all mice in the control had to be euthanised due to large tumor mass. In the P815-1/PLG1 immunized group; however, 7 out of 10 mice were free from tumor and of the remaining mice, tumor progression was significantly slower than in the control groups. Those mice which have rejected tumors upon pre-immunization with P815-1/PLG1 remained tumor free for over 90 days. The results, summarized in FIG. 5, demonstrate that the immunity elicited in vivo by a tumor associated antigen encapsulated in PLG1 may be potent enough to protect against the challenge of a malignant metastatic tumor like P815.

Blend COMPONENT ENCAPSULATED ANTIGENS

Using the procedures described above in Examples 8–11, the blend component system was tested in order to determine if it would elicit an immune response. The encapsulated bioactive agents used in the study were prepared in Examples 3–4. The results are shown in FIGS. 6a–i.

Example 12

To address whether the bioactive agents encapsulated in the blend component system of the present invention could also elicit specific CTL in vivo, C57BL/6 mice were immunized subcutaneously with 30 ig/mouse of Ova encapsulated in different formulations of PLG (Table 1). Two weeks later, mice were sacrificed and spleen cells were prepared for in vitro stimulation with irradiated EG7.Ova as described above.

The data shown in FIGS. 6a–i demonstrates that the blend component system composed of a blend of high and low MW polymers have the capacity in vivo to efficiently prime Class I restricted CTL. The effect of various ratios of high to low MW polymers were tested for effective CTL priming. C57BL/6 mice ($H\text{-}2^b$) were immunized with either soluble Ova or several Ova/PLG formulations composed of high and low MW polymers in ratios ranging from 80–60% of high MW and 20–40% of low MW.

The blend component system of the present invention exhibited a consistent CTL response. In the case of the prior art single component systems, inconsistent CTL responses were observed. Depending upon the conditions in which the single component system was prepared, the kinetics of release of the prior art single component systems may vary. The incorporation of component (b) in the blend component system alleviates this problem, which results in a consistent and higher kinetics of release of the bioactive agent. Additionally, the single component system of the invention exhibited a higher consistency of CTL response than the prior art single component system.

TABLE 1

| Graph | Component (a) (mole % ratio of lactide/glycolide) | Amount of Component (a), (weight %) | I.V. of Component (a) (dL/g) | Component (b) Amount of 100% polylactide[1] (weight %) | Surfactant[4] |
|---|---|---|---|---|---|
| a[2] | — | — | — | — | — |
| b | 60/40 PLG | 80 | 0.49 | 20 | CMC/Tween 80 |
| c | 60/40 PLG | 80 | 0.49 | 20 | CMC/PVA |

TABLE 1-continued

| Graph | Component (a) (mole % ratio of lactide/glycolide) | Amount of Component (a), (weight %) | I.V. of Component (a) (dL/g) | Component (b) Amount of 100% polylactide[1] (weight %) | Surfactant[4] |
|---|---|---|---|---|---|
| d | 60/40 PLG | 70 | 0.49 | 30 | CMC/PVA |
| e | 60/40 PLG | 60 | 0.49 | 40 | CMC/PVA |
| f | 50/50 PLG[3] | 85 | 0.39 | 15 | CMC/PVA |
| g | 50/50 PLG | 95 | 0.39 | 5 | CMC/PVA |
| h | 50/50 PLG | 90 | 0.39 | 10 | CMC/PVA |
| i | 50/50 PLG | 80 | 0.39 | 20 | CMC/PVA |

[1]The molecular weight of the polylactide was 2000 daltons.
[2]Graph (a) was a control experiment using phosphate buffer saline.
[3]The 50/50 PLG in run (f) was unblocked. Components (a) for Graphs b–e and g–i and the polylactide (component (b)) are blocked.
[4]CMC is carboxymethyl cellulose and PVA is poly(vinyl alcohol).

Example 13

To demonstrate that microspheres of the present invention induce a stronger and faster CTL response, the following experiment was performed. To address whether microspheres that degrade at an accelerated rate induce a stronger and faster CTL response, the following experiment was performed. Pursuant to the invention, the addition of low molecular weight components to higher molecular weight PLG enhances the release of drugs encapsulated in the microspheres. All PLG formulations were produced by Southern Research Institute (Birmingham, Ala.).

Two batches of microspheres containing ovalbumin (grade VII), (Sigma, St. Louis, Mo.) were prepared, one consisting of 65:35 PLG polymer (Boehringer Ingelheim, Petersburg, Va.), the other consisting of 65:35 PLG blended with 40% (by weight) of R104 lactide (2000 kD) (Boehringer Ingelheim).

Batch J236-134-00 made with a single polymer

Ovalbumin (5.15 mg, Grade VII, Sigma, St. Louis, Mo.) was dissolved in sterile water to make a solution containing 20 mg ovalbumin/ml. This ovalbumin solution was pulled into a 1-cc syringe having an 18-guage needle.

A polymer solution was made by dissolving 0.50 g 65:35 DL-PLG (inherent viscosity of 0.72 dl/gm, methylene chloride) in 6.3 g methylene chloride. This polymer solution was poured into a capped 10-cc syringe. Next, the polymer solution was mixed with a Brinkman Polytron homogenizer. During this mixing, the ovalbumin solution was added to the polymer solution to form a water-in-oil (w/o) emulsion. The emulsion was mixed for a total of 45 seconds (15-second intervals). After mixing, a 14-guage needle was placed on the end of the 10-cc syringe.

Next the w/o emulsion was injected from the 10-cc syringe through the 14-gauge needle into 280 ml of a 1.4 wt % aqueous solution of carboxymethyl cellulose (CMC) saturated with methylene chloride. During this addition of the w/o emulsion, the 1.4 wt % CMC was stirred at 4008 rpm with a Silverson Homogenizer to form a water-in-oil-water (w/o/w) emulsion. The w/o/w emulsion was mixed for 75 seconds. After 75 seconds of mixing, the w/o/w was rapidly poured into 3.5 l of sterile water to form solid particles (microspheres). During this addition, the 3.5 l sterile water was stirred at ~600 rpm with a Cole-Parmer laboratory stirrer. The mixture was stirred for 18 minutes.

The suspension of microspheres was divided between four 800-ml bottles and spun for 35 minutes in a Beckman J6-M centrifuge. After removing the supernatant, the microspheres were transferred to two 800-ml bottles. About 800 ml of sterile water was added to each bottle to resuspend the microspheres. The suspensions were spun for 70 minutes. After spinning, the supernatants were removed and 125 ml of sterile water was added to each 800-ml bottle and the microspheres were resuspended. Next, the suspensions were combined in a 500-ml freeze-drying flask along with 0.3447 g Biotech grade mannitol. After the mannitol was dissolved, the suspension was frozen and lyophilized.

The resultant microspheres contained 0.88 wt % ovalbumin and were about 1 to 10 micron in diameter.

Batch J236-149-00 made with a 60/40 blend of two polymers

Ovalbumin (5.31 mg, Grade VII, Sigma, St. Louis, Mo.) was dissolved in sterile water to make a solution containing 20 mg ovalbumin/ml. This ovalbumin solution was pulled into a 1-cc syringe having an 18-guage needle.

A polymer solution was made by dissolving 0.30 g 65:35 DL-PLG (inherent viscosity of 0.72 dl/gm, methylene chloride) and 0.21 g of poly(DL-lactide) (2000 dalton, R104, Boehringer Ingelheim) in 6.3 g methylene chloride. This polymer solution was poured into a capped 10-cc syringe. Next, the polymer solution was mixed with a Brinkman Polytron homogenizer. During this mixing, the ovalbumin solution was added to the polymer solution to form a water-in-oil (w/o) emulsion. The emulsion was mixed for a total of 45 seconds (15-second intervals). After mixing, a 14-guage needle was placed on the end of the 10-cc syringe.

Next the w/o emulsion was injected from the 10-cc syringe through the 14-gauge needle into 280 ml of a 1.4 wt % aqueous solution of carboxymethyl cellulose (CMC) saturated with methylene chloride. During this addition of the w/o emulsion, the 1.4 wt % CMC was stirred at 3867 rpm with a Silverson Homogenizer to form a water-in-oil-water (w/o/w) emulsion. The w/o/w emulsion was mixed for 75 seconds. After 75 seconds of mixing, the w/o/w was rapidly poured into 3.5 l of sterile water to form solid particles (microspheres). During this addition, the 3.5 l sterile water was stirred at ~600 rpm with a Cole-Parmer laboratory stirrer. The mixture was stirred for 20 minutes.

The suspension of microspheres was divided between four 800-ml bottles and spun for 35 minutes in a Beckman J6-M centrifuge. After removing the supernatant, the microspheres were transferred to two 800-ml bottles. About 800 ml of sterile water was added to each bottle to resuspend the microspheres. The suspensions were spun for 70 minutes. After spinning, the supernatants were removed and 125 ml of sterile water was added to each 800-ml bottle and the microspheres were resuspended. Next, the suspensions were combined in a 500-ml freeze-drying flask along with 0.3447 g Biotech grade mannitol. After the mannitol was dissolved, the suspension was frozen and lyophilized.

The resultant microspheres contained 0.83 wt % ovalbumin and were about 1 to 10 micron in diameter. The microspheres were characterized using standard methods to determine core loading, homogeneity of encapsulated protein and in vitro release characteristics of the microspheres.

Tissue cultures used an RPMI complete medium supplemented with 10% FCS, 2 mM glutamine, 50 U/ml penicillin, streptomycin, gentamycin and 2'10-5 M 2-mercaptoethanol. A EL4 thymoma cell line (ATCC, Rockville, Md.), transfected with ovalbumin (EG7.Ova), was grown in a selective medium containing 0.4 mg/ml G418. C57BL/6 mice (Charles River Laboratories, Boston, Mass.) (3 per group) were immunized subcutaneously with 30 $\mu$g ovalbumin encapsulated in the PLG microspheres. The microspheres were suspended in 200 $\mu$L of phosphate buffered saline and administered on both flanks of the animals. After 10 days, splenocytes were prepared as single cell suspensions and ca. 50'106 cells from each mouse were incubated with 2.5'106 irradiated (200,000 rad) EG7.Ova cells.

After five days of culture, CTL activities were measured using a 51Cr release cytotoxicity assay. Target cells (EG7.Ova or untransfected EL4) were incubated with 51Cr at 100 $\mu$Ci/106 cells at 37° C. for 60 min. Labeled cells were washed 2 or 3 times and 1'104 labeled target cells per well were distributed into 96 well plates in a final volume of 200 $\mu$l/well of RP-10 (RPMI medium with 10% FCS). Effector-:target ratios are as indicated on FIGS. 7a–b. After 4 hours of incubation at 37° C., supernatant was collected from test wells using Skatron filter strips and counted on a Packard Cobra II gamma counter. Specific lysis was determined as:

$$\% \text{ specific lysis} = \frac{\text{Experimental release} - \text{Spontaneous release}}{\text{Maximum release} - \text{Spontaneous release}} \times 100$$

Figure 7A:
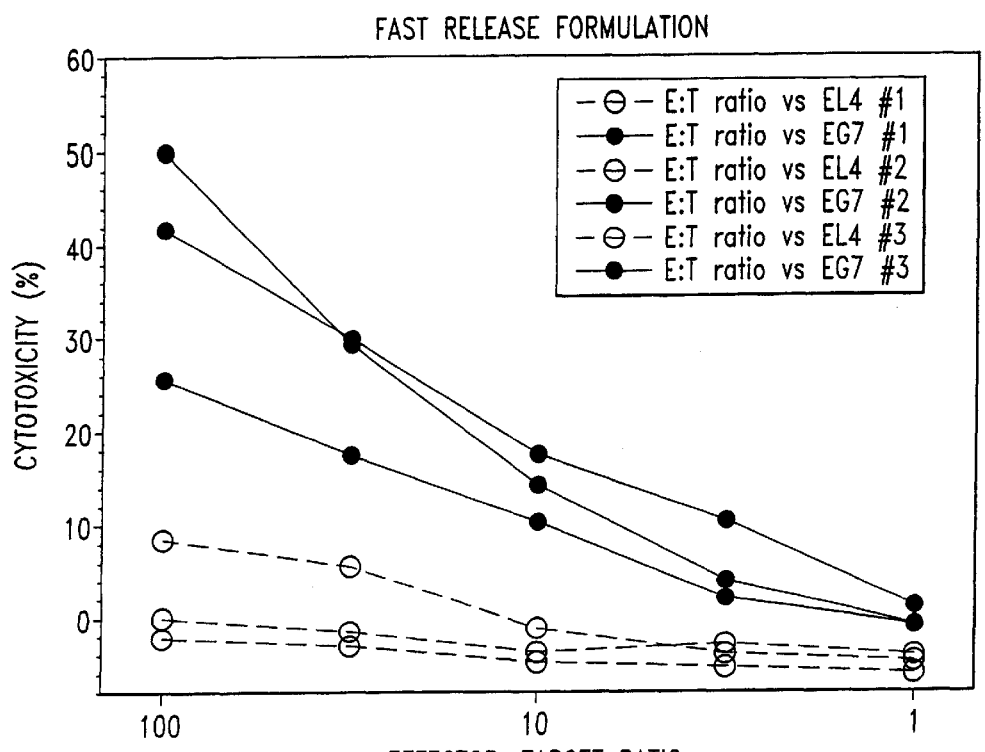
Figure 7B:
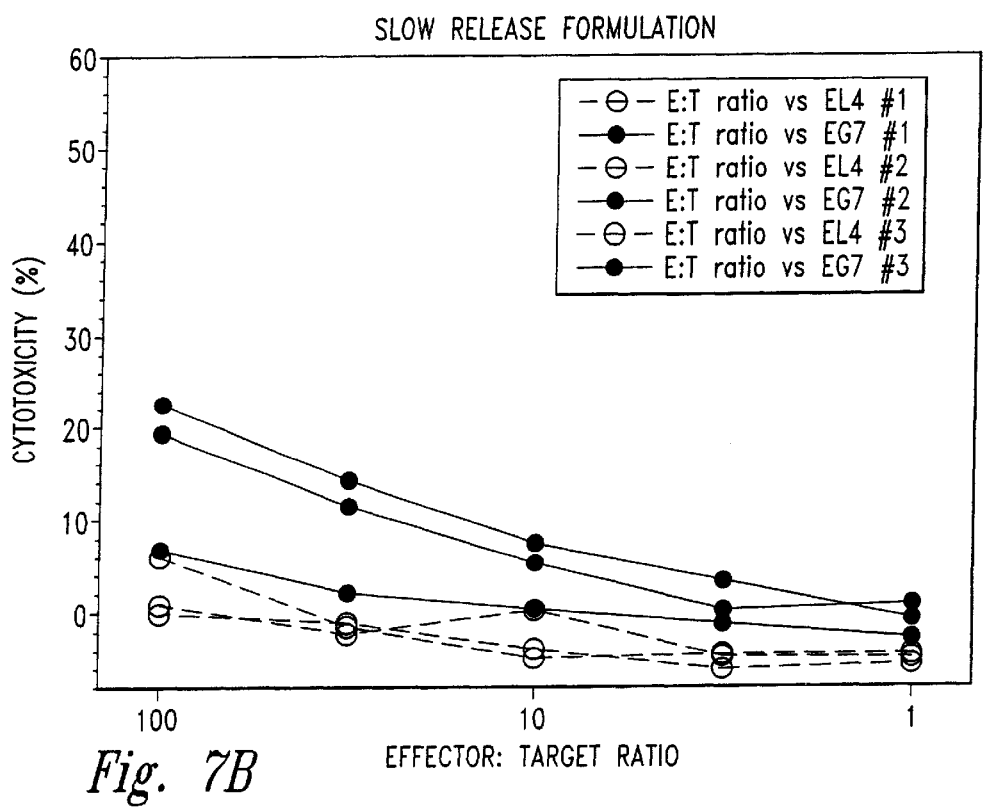

The data shown in FIGS. 7a–b show the % lysis obtained using the two microsphere preparations. FIG. 7a shows data from the 65:35 PLG microspheres over various effector:target ratios and FIG. 7b shows data obtained with the 65:35 PLG blended with 40% by weight R104 lactide. The responses for individual mice are shown against both EG7.Ova and untransfected EL4 cells. Lysis of EG7.Ova cells was significantly higher from mice immunized with the polymer blend compared to mice immunized with the 65:35 PLG alone.

Example 14

To demonstrate that microspheres made from polymer blend induce antigen specific T helper responses in vivo, the MtB antigen, 85b, was encapsulated in a blend of 80% 60:40 PLG and 20% R104 lactide. All PLG formulations were produced by Southern Research Institute according to the methods of Example 13.

Balb/c mice (female, 6–8 weeks old, Charles River Laboratories, Boston, Mass.) were immunized s.c. in the flanks with the following immunization reagents: 85b/PLG microspheres (containing 40 mg of 85b in a final volume of 200 ml of sterile PBS (Gibco BRL)), placebo PLG microspheres containing no antigen or PBS. Animals were boosted with the same dose on day 14 before being sacrificed on day 28. Single cell suspensions of the pooled spleens were prepared and resuspended at 3×10⁶ cells/ml in complete media (RPMI-1640, containing 10% FCS, 2 mM glutamine, sodium pyruvate, non-essential amino acids, 2×10⁻⁵ M 2-mecaptoethanol, 50 U/ml penicillin and streptomycin). The spleen cells (3×10⁵ cells per well) were then stimulated in vitro (triplicate wells) 20, 10 or 5 mg/ml of soluble recombinant 85b. Cells were stimulated for 5 days at 37 C. in the presence of 5% $CO_2$. Cells were pulsed with $^3$[H]thymidine (Amersham, Mass., 1 mCu per well) for the last 18 hours of culture, then harvested using a Packard filtermate 196. Thymidine incorporation was evaluated using a Packard Beta counter. Results, expressed as stimulation indices, were determined from the following equation:

$$\text{Stimulation Index} = \frac{\text{Mean } CPM \text{ of antigen stimulated wells}}{\text{Mean } CPM \text{ for media stimulated wells}}$$

The results (Table 2) show that 85b incorporated into a blend of 80% 60:40 PLG and 20% R104 lactide resulted in an antigen specific splenic proliferative response. The 85b/PLG microspheres induced responses significantly higher than for either placebo microsphere or PBS immunized mice.

TABLE 2

| Immunization Reagent | T helper Stimulation Index | | |
|---|---|---|---|
| | 5 $\mu$g/ml 85b | 10 $\mu$g/ml 85b | 20 $\mu$g/ml 85b |
| PBS | 1.2 | 3.03 | 4.5 |
| Placebo: 80% 60:40 PLG 20% R104 | 1.8 | 2.2 | 5.7 |
| 85b encapsulated in 80% 60:40 PLG/20% R104 | 19.5 | 16.4 | 13.8 |

Although the present process has been described with reference to specific details of certain embodiments thereof, it is not intended that such details should be regarded as limitations upon the scope of the invention except as and to the extent that they are included in the accompanying claims.

What is claimed is:

1. A method of inducing or potentiating a CTL response in a subject, comprising administering to the subject an effective amount of a composition comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition thereby inducing or potentiating the CTL response in the subject.

2. The method of claim 1 wherein the polymeric composition provides kinetics of antigen or nucleic acid release such that a CTL response is measurable within fourteen days of a single administration at a level of at least 30% cytotoxicity.

3. The method of claim 1 wherein component (b) comprises a rapidly dissolving component.

4. The method of claim 1 wherein component (a) and component (b) or both comprises a biodegradable polymer.

5. The method of claim 1 wherein the CTL response is measurable within seven days of a single administration.

6. The method of claim 1 wherein the composition further comprises an adjuvant.

7. The method of claim 1 wherein component (a) and/or (b) comprises a poly(lactide-co-glycolide), poly(lactide), poly(glycolide), copolyoxalate, polycaprolactone, poly(lactide-co-caprolactone), poly(esteramide), polyorthoester, poly(a-hydroxybutyric acid), polyanhydride, or a mixture thereof.

8. The method of claim 1 wherein component (a) comprises a polymer formed from components comprising 40 to 100 mole % lactide and from 0 to 60 mole % glycolide.

9. The method of claim 1 wherein component (a) is 60:40 poly(lactide-co-glycolide).

10. The method of claim 1 wherein component (a) is 50:50 poly(lactide-co-glycolide).

11. The method of claim 1 wherein component (b) comprises a polymer formed from components comprising 0 to 100 mole % lactide and from 0 to 100 mole % glycolide.

12. The method of claim 1 wherein component (b) is homopolymer of poly(lactide).

13. The method of claim 1 wherein component (a) is from 60:40 to 50:50 poly(lactide-co-glycolide) and has an inherent viscosity of from 0.39 to 0.49 dL/g in hexafluoroisopropanol and component (b) is homopolymer of poly(lactide) having a molecular weight of 2000 daltons.

14. The method of claim 1 wherein component (b) has a molecular weight less than component (a).

15. The method of claim 1 wherein the composition further comprises a component (b) selected from the group consisting of carboxymethyl cellulose, gelatin, poly(vinyl pyrrolidone), polyethylene glycol, Tween 80, Tween 20 and mixture thereof.

16. The method of claim 1 wherein the polymeric composition is a microparticle, microcapsule, microsphere, nanoparticle, nanocapsule or nanosphere.

17. The method of claim 1 wherein the polymeric composition is less than or equal to 10 im in average diameter.

18. The method of claim 1 wherein the polymeric composition is less than or equal to 5 im in average diameter.

19. The method of claim 1 wherein the polymeric composition is from about 1 im to about 10 im in average diameter.

20. The method of claim 1 wherein the composition is administered rectally, vaginally, nasally, orally, opthamalically, transdermally, intradermally, topically, parenterally or by inhalation.

21. The method of claim 1 wherein the composition is administered parenterally.

22. The method of claim 1 wherein the dosage of the antigen or nucleic acid encoding the antigen is from 1 ng to 100 mg.

23. The method of claim 1 wherein the subject is a mammal.

24. A composition for inducing or potentiating a CTL response in a subject, comprising an antigen or a nucleic acid encoding the antigen, encapsulated in a polymeric composition, wherein the polymeric composition comprises a blend of
   (a) a polymer present in an amount sufficient to provide structural integrity to the polymeric composition, and
   (b) a component selected from the group consisting of a rapidly biodegradable component, a rapidly dissolving component, a rapidly swelling component, and a component that causes osmotic rupture of the encapsulated polymeric composition thereby inducing or potentiating the CTL response in the subject.

25. The composition of claim 24 wherein the polymeric composition provides kinetics of antigen or nucleic acid release such that a CTL response is measurable within fourteen days of a single administration at a level of at least 30% cytotoxicity.

26. The composition of claim 24 wherein the composition further comprises a bioactive agent capable of potentiating the CTL response encapsulated in a second polymeric composition, wherein the second polymeric composition comprises components (a) and/or (b).

27. The composition of claim 24 wherein the CTL response is measurable within seven days of a single administration.

28. The composition of claim 24 wherein component (b) comprises a rapidly dissolving component.

29. The composition of claim 24 wherein component (a) and component (b) or both comprises a biodegradable polymer.

30. The composition of claim 24 wherein the composition further comprises an adjuvant.

31. The composition of claim 24 wherein component (a) and/or (b) comprises a poly(lactide-co-glycolide), poly(lactide), poly(glycolide), copolyoxalate, polycaprolactone, poly(lactide-co-caprolactone), poly(esteramide), polyorthoester, poly(a-hydroxybutyric acid), polyanhydride, or a mixture thereof.

32. The composition of claim 24 wherein component (a) comprises a polymer formed from components comprising 40 to 100 mole % lactide and from 0 to 60 mole % glycolide.

33. The composition of claim 24 wherein component (a) is 60:40 poly(lactide-co-glycolide).

34. The composition of claim 24 wherein component (a) is 50:50 poly(lactide-co-glycolide).

35. The composition of claim 24 wherein component (b) comprises a polymer formed from components comprising 0 to 100 mole % lactide and from 0 to 100 mole % glycolide.

36. The composition of claim 24 wherein component (b) is homopolymer of poly(lactide).

37. The composition of claim 24 wherein component (a) is from 60:40 to 50:50 poly(lactide-co-glycolide) and has an inherent viscosity of from 0.39 to 0.49 dL/g in hexafluoroisopropanol and component (b) is homopolymer of poly(lactide) having a molecular weight of 2000 daltons.

38. The composition of claim 24 wherein component (b) has a molecular weight less than component (a).

39. The composition of claim 24 wherein the composition further comprises a component (b) selected from the group consisting of carboxymethyl cellulose, gelatin, poly(vinyl pyrrolidone), polyethylene glycol, Tween 80, Tween 20 or mixture thereof.

40. The composition of claim 24 wherein the polymeric composition is a microparticle, microcapsule, microsphere, nanoparticle, nanocapsule or nanosphere.

41. The composition of claim 24 wherein the polymeric composition is less than or equal to 10 im in average diameter.

42. The composition of claim 24 wherein the polymeric composition is less than or equal to 5 im in average diameter.

43. The composition of claim 24 wherein the polymeric composition is from about 1 im to about 10 im in average diameter.

44. The composition of claim 24 wherein the polymeric composition further comprises a pharmaceutically acceptable carrier.

45. A method of inducing or potentiating a T helper cell response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

46. The method of claim 45 wherein the polymeric composition provides kinetics of antigen or nucleic acid release such that a T helper cell response is measurable within fourteen days of a single administration at a level of at least two-fold over background as measured by T cell proliferation or cytokine induction, thereby inducing the T helper cell response in the subject.

47. A composition for inducing or potentiating a T helper cell response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, or a component that causes osmotic rupture of the encapsulated polymeric composition.

48. The composition of claim 47 wherein the polymeric composition provides kinetics of antigen or nucleic acid release such that a T helper cell response is measurable within fourteen days of a single administration at a level of at least two-fold over background.

49. A method of inducing or potentiating a neutralizing antibody response in a subject, comprising administering to the subject an effective amount of a composition comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, or a component that causes osmotic rupture of the encapsulated polymeric compositionthereby inducing the neutralizing antibody response in the subject.

50. The method of claim 49 wherein the polymeric composition provides kinetics of antigen or nucleic acid release such that the neutralizing antibody response is detectable within thirty days of a second or subsequent administration.

51. The method of claim 49 wherein the neutralizing antibody response is dectable within fourteen days.

52. A composition for inducing or potentiating a neutralizing antibody response in a subject, comprising an antigen or a nucleic acid encoding the antigen, encapsulated in a polymeric composition, wherein the polymeric composition comprises a blend of (a) a polymer present in an amount sufficient to provide structural integrity to the polymeric composition, and (b) a component selected from the group consisting of a rapidly biodegradable component, a rapidly dissolving component, a rapidly swelling component, and a component that causes osmotic rupture of the encapsulated polymeric composition.

53. The composition of claim 52 wherein the polymeric composition provides kinetics of antigen or nucleic acid release such that the neutralizing antibody response is detectable within thirty days of a second or subsequent administration.

54. The composition of claim 53 wherein the neutralizing antibody response is detectable within fourteen days of a second or subsequent administration.

55. The composition of claim 52 wherein the neutralizing antibody response is detectable within ten days of a second or subsequent administration.

56. The composition of claim 52 wherein the polymeric further comprises a pharmaceutically acceptable carrier.

\* \* \* \* \*

UNITED STATES PATENT AND TRADEMARK OFFICE
CERTIFICATE OF CORRECTION

PATENT NO. : 6,312,731 B1
DATED : November 6, 2005
INVENTOR(S) : Staas et al.

It is certified that error appears in the above-identified patent and that said Letters Patent is hereby corrected as shown below:

Title page,
Item [56], References Cited, U.S. PATENT DOCUMENTS, please insert the following:

| | | |
|---|---|---|
| -- 4,675,189 | 06/23/1987 | Kent et al. |
| 5,019,400 | 05/28/1991 | Gombotz et al. |
| 5,100,664 | 03/31/1992 | Doyle et al. |
| 5,100,669 | 03/31/1992 | Hyon et al. |
| 5,384,133 | 01/24/1995 | Boyes et al. |
| 5,407,609 | 04/18/1995 | Tice et al. |
| 5,417,986 | 05/23/1995 | Reid et al. --. |

FOREIGN PATENT DOCUMENTS, please insert the following:

| | | |
|---|---|---|
| -- EP 0058481 B1 | 10/01/1986 | Imperial Chemical Industries PLC |
| EP 0706792 A1 | 04/17/1996 | The UAB Research Foundation |
| WO 94/07469 | 04/14/1994 | Dynagen, Inc. |
| WO 94/12158 | 06/09/1994 | Alkermes Controlled Therapeutics, Inc. |
| WO 94/15636 | 07/21/1994 | CSL Limited |
| WO 94/27718 | 12/08/1994 | O'Hagan |
| WO 95/11010 | 04/27/1995 | Genentech, Inc. |
| WO 95/28149 | 10/26/1995 | Pierre Fabre Medicament |
| WO 96/40066 | 12/19/1996 | The Governors of the University of Alberta |
| WO 97/13502 | 04/17/1997 | Immunex Corporation --. |

OTHER PUBLICATIONS, please insert the following:

-- Conway et al., "Double Emulsion Microencapsulation of Proteins as Model Antigens Using Polylactide Polymers: Effect of Emulsifier on the Microsphere Characteristics and Release Kinetics," Eur. J. Pharm. Biopharm. 42(1):42-48 (1996).

Ertl et al., "Poly(DL-lactide-Co-Glycolide) Microspheres as Carriers for Peptide Vaccines," Vaccine, 14(9): 879-885 (1996).

Grandfils et al., "Control of the Biodegradation Rate of Poly(DL-lactide) Microparticles Intended As Chemoembolization Materials," Journal of Controlled Release 38:109-122 (1996).

Hermann et al., "Somatostatin Containing Biodegradable Microspheres Prepared by a Modified Solvent Evaporation Method Based On W/O/W-Multiple Emulsions," International Journal of Pharmaceutics 126:129-138 (1995).

Men et al., "A Single Administration of Tetanus Toxoid in Biodegradable Microspheres Elicits T Cell and Antibody Responses Similar or Superior to those obtained with Aluminum Hydroxide," Vaccine, 13(7):683-689 (1995).

Moore et al., "Immunization with a Soluble Recombinant HIV Protein Entrapped in Biodegradable Microparticles Induces HIV-Specific $CD8^+$ Cytotoxic T Lymphocytes and $CD4^+$ Th1 Cells," Vaccine, 13(18):1741-1749 (1995).

O'Hagan et al., "Biodegradable Microparticles As Oral Vaccines," Adv. Exp. Med. Biol., pp. 1463-1467 (1995).

UNITED STATES PATENT AND TRADEMARK OFFICE
CERTIFICATE OF CORRECTION

PATENT NO. : 6,312,731 B1
DATED : November 6, 2005
INVENTOR(S) : Staas et al.

It is certified that error appears in the above-identified patent and that said Letters Patent is hereby corrected as shown below:

Title page (cont'd),

Tabata et al., "Protein Precoating of Polylactide Microspheres Containing a Lipophilic Immunopotentiator for Enhancement of Macrophage Phagocytosis and Activation," Pharmaceutical Research, 6(4):296-301 (1989).

Thomasin et al., "Tetanus Toxoid and Synthetic Malaria Antigen Containing Poly(Lactide-Co-Glycolide) Microspheres: Importance of Polymer Degradation and Antigen Release for Immune Response," Journal of Controlled Release 41:131-145 (1996).

Yeh et al., "Improving the Delivery Capacity of Microparticle Systems Using Blends of Poly(DL-Lactide Co-Glycolide) and Poly(Ethyleneglycol)," Journal of Controlled Release 37:1-9 (1995).

Yeh et al., "Improving Protein Delivery from Microparticles Using Blends of Poly(DL-lactide co-glycolide) and Poly(ethylene oxide)-Poly(propylene Oxide) Copolymers," Pharmaceutical Research, 13(11)1693-1698 (1996). --.

Signed and Sealed this

Eighteenth Day of October, 2005

JON W. DUDAS
*Director of the United States Patent and Trademark Office*